(12) United States Patent
Karlsson et al.

(10) Patent No.: US 10,077,320 B2
(45) Date of Patent: Sep. 18, 2018

(54) PROCESS FOR PREPARING A CROSS-LINKED HYALURONIC ACID PRODUCT

(71) Applicant: GALDERMA S.A., Cham (CH)

(72) Inventors: Morgan Karlsson, Knivsta (SE); Katarina Edsman, Alunda (SE)

(73) Assignee: GALDERMA S.A., Cham (CH)

( * ) Notice: Subject to any disclaimer, the term of this patent is extended or adjusted under 35 U.S.C. 154(b) by 0 days.

(21) Appl. No.: 14/901,462

(22) PCT Filed: Jun. 5, 2014

(86) PCT No.: PCT/EP2014/061674
§ 371 (c)(1),
(2) Date: Dec. 28, 2015

(87) PCT Pub. No.: WO2014/206701
PCT Pub. Date: Dec. 31, 2014

(65) Prior Publication Data
US 2016/0376382 A1 Dec. 29, 2016

(30) Foreign Application Priority Data

Jun. 28, 2013 (WO) ................. PCT/EP2013/063718

(51) Int. Cl.
| | |
|---|---|
| *C08B 37/08* | (2006.01) |
| *C08J 3/075* | (2006.01) |
| *C08J 3/24* | (2006.01) |
| *A61K 9/06* | (2006.01) |
| *A61K 8/04* | (2006.01) |
| *A61Q 19/00* | (2006.01) |
| *A61K 8/73* | (2006.01) |
| *A61K 31/728* | (2006.01) |

(52) U.S. Cl.
CPC .......... *C08B 37/0072* (2013.01); *A61K 8/042* (2013.01); *A61K 8/735* (2013.01); *A61K 9/06* (2013.01); *A61K 31/728* (2013.01); *A61Q 19/00* (2013.01); *C08J 3/075* (2013.01); *C08J 3/244* (2013.01); *C08J 2305/08* (2013.01)

(58) Field of Classification Search
CPC ........ C08B 37/0072; C08J 3/075; C08J 3/244
See application file for complete search history.

(56) References Cited

U.S. PATENT DOCUMENTS

| | | | |
|---|---|---|---|
| 4,716,224 A | * | 12/1987 | Sakurai .................. A61K 8/735 514/825 |
| 4,963,666 A | | 10/1990 | Malson |
| 6,831,172 B1 | | 12/2004 | Barbucci et al. |
| 6,921,819 B2 | * | 7/2005 | Piron ..................... A61K 8/042 536/106 |
| 2002/0091251 A1 | | 7/2002 | Zhao |
| 2006/0057098 A1 | | 3/2006 | Sato |
| 2006/0105022 A1 | | 5/2006 | Yokokawa et al. |

FOREIGN PATENT DOCUMENTS

| | | |
|---|---|---|
| CN | 101056891 A | 10/2007 |
| EP | 1 837 347 A1 | 9/2007 |
| JP | 2002529550 A | 9/2002 |
| JP | 2006111867 A | 4/2006 |
| WO | WO 87/07898 A1 | 12/1987 |
| WO | WO 00/46253 A1 | 8/2000 |

OTHER PUBLICATIONS

International Preliminary Patentability Report (IPRP) with Written Opinion dated Jan. 7, 2016, in corresponding International Application No. PCT/EP2014/061674.
International Search Report (PCT/ISA/210) dated Aug. 6, 2014, by the European Patent Office as the International Searching Authority for International Application No. PCT/EP2014/061674.
Written Opinion (PCT/ISA/237) dated Aug. 6, 2014, by the European Patent Office as the International Searching Authority for International Application No. PCT/EP2014/061674.
International Search Report (PCT/ISA/210) dated Aug. 6, 2014, by the Japanese Patent Office as the International Searching Authority for International Application No. PCT/EP2014/061674.
Written Opinion (PCT/ISA/237) dated Aug. 6, 2014, by the Japanese Patent Office as the International Searching Authority for International Application No. PCT/EP2014/061674.
Office Action (Notification of Reasons for Refusal) dated Feb. 8, 2018, by the Japanese Patent Office in Japanese Patent Application No. 2016-522367, and an English Translation of the Office Action. (9 pages).

* cited by examiner

*Primary Examiner* — Jonathan S Lau
(74) *Attorney, Agent, or Firm* — Buchanan Ingersoll & Rooney LLP

(57) ABSTRACT

Efficient cross-linking of hyaluronic acid (HA) is provided by a manufacturing process. In the process, HA is activated by an initial cross-linking in an aqueous solution. Unreacted cross-linking agent is removed from the activated HA. Cross-linking of the activated HA is finalized, without addition of any additional cross-linking agent, in a suspension of a liquid precipitating medium and the activated HA in precipitated form. The resulting cross-linked HA products exhibit high effective cross-linker ratio and other favorable properties, making the products useful as implants and in medical and cosmetic surgery.

16 Claims, 5 Drawing Sheets

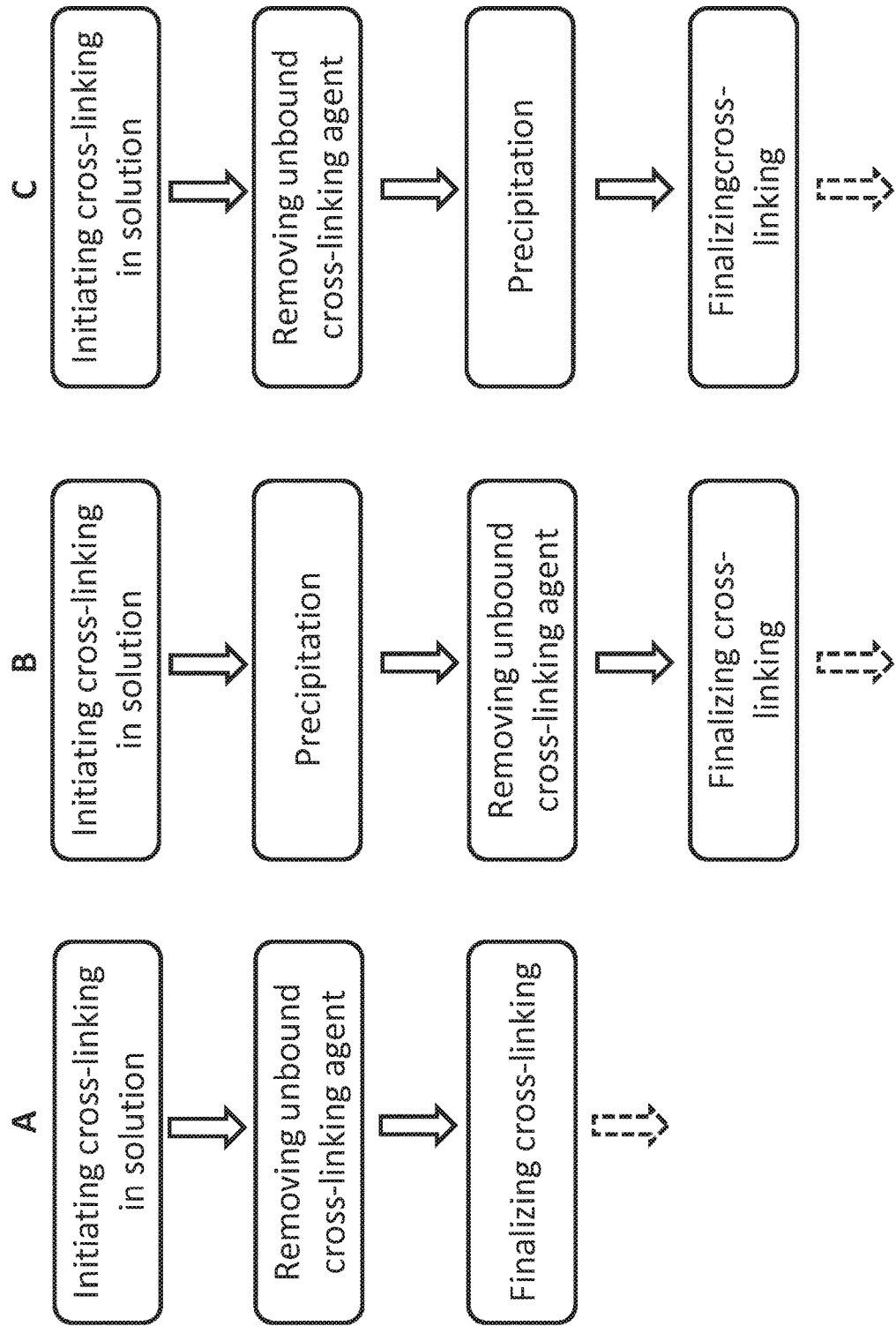

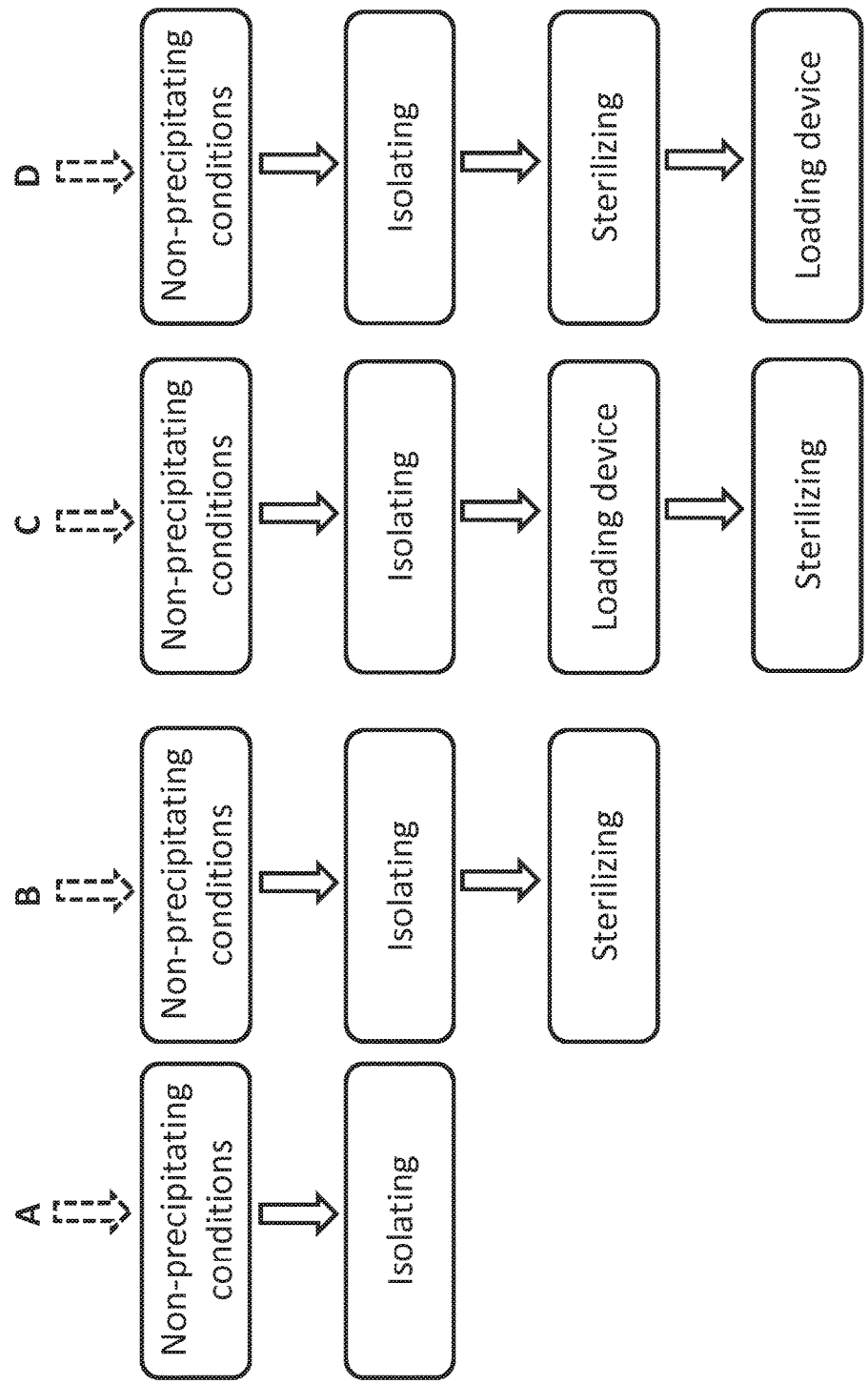

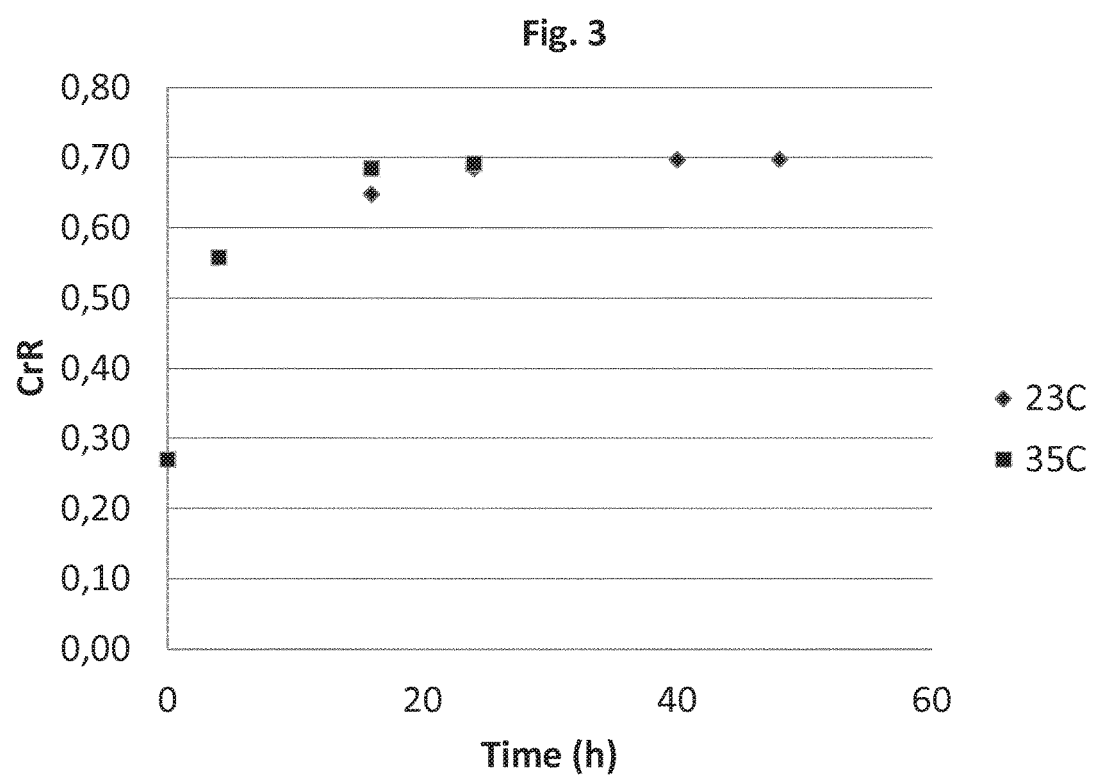

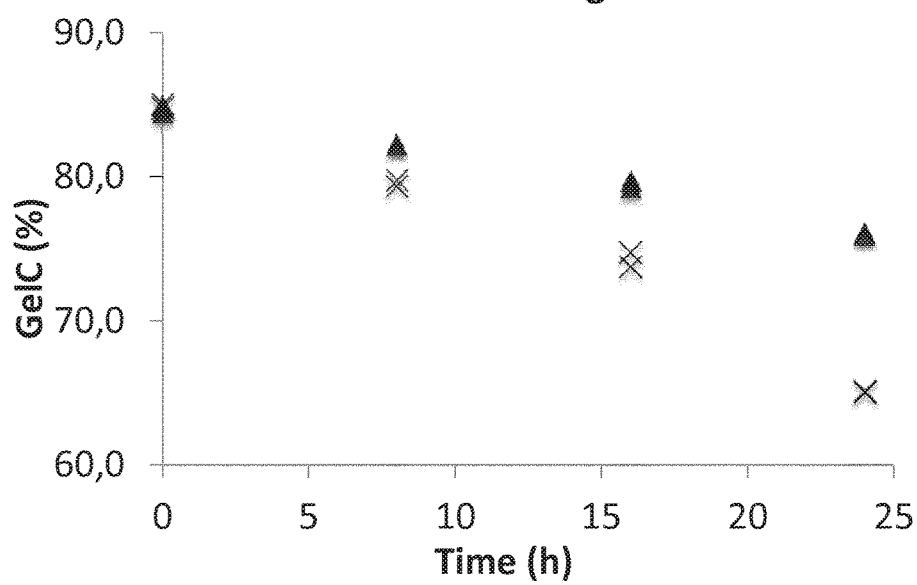
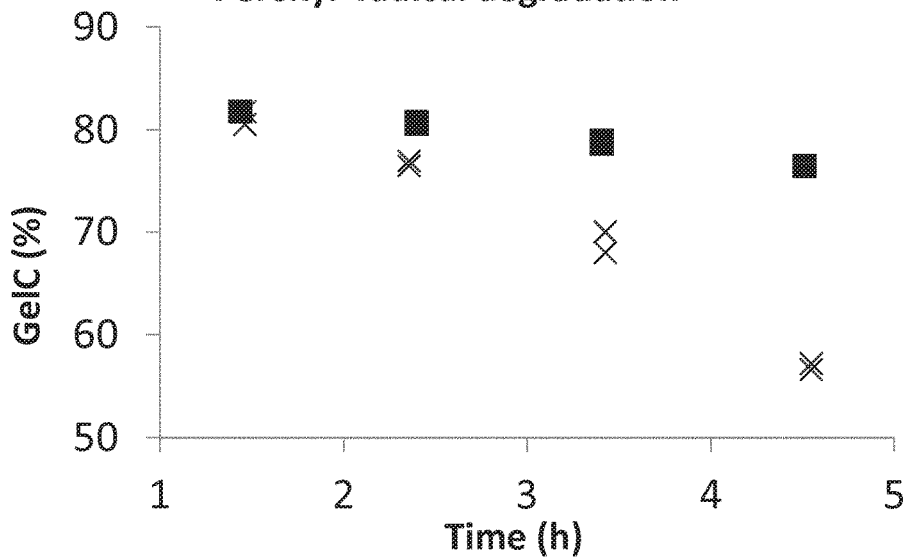

US 10,077,320 B2

PROCESS FOR PREPARING A CROSS-LINKED HYALURONIC ACID PRODUCT

FIELD OF THE INVENTION

The present invention relates to the field of polysaccharides. More specifically, the present invention is concerned with novel processes of cross-linking hyaluronic acid (HA) and of manufacturing cross-linked HA products.

BACKGROUND OF THE INVENTION

One of the most widely used biocompatible polymers for medical use is hyaluronic acid (HA). It is a naturally occurring polysaccharide belonging to the group of glycosaminoglycans (GAGs). HA and the other GAGs are negatively charged heteropolysaccharide chains which have a capacity to absorb large amounts of water. HA and products derived from HA are widely used in the biomedical and cosmetic fields, for instance during viscosurgery and as a dermal filler.

Water-absorbing gels, or hydrogels, are widely used in the biomedical field. They are generally prepared by chemical cross-linking of polymers to infinite networks. While native HA and certain cross-linked HA products absorb water until they are completely dissolved, cross-linked HA gels typically absorb a certain amount of water until they are saturated, i.e. they have a finite liquid retention capacity, or swelling degree.

Since HA is present with identical chemical structure except for its molecular mass in most living organisms, it gives a minimum of reactions and allows for advanced medical uses. Cross-linking and/or other modifications of the HA molecule is necessary to improve its resistance to degradation or duration in vivo. Furthermore, such modifications affect the liquid retention capacity of the HA molecule. As a consequence thereof, HA has been the subject of many modification attempts.

When preparing gels from biocompatible polymers, it is advantageous to ensure a low degree of cross-linking so as to maintain a high bio-compatibility. However, often a more dense gel is required to have a proper biomedical effect, and in such a case the biocompatibility will often be lost.

Some known soft-tissue augmentation treatments involving implants occasionally suffer from the drawback that the implant, or part thereof, migrates away from the desired site of treatment.

WO 87/07898 discloses a method for preparing HA films. Any gel formation shall be avoided until the cross-linking step, which involves drying of an aqueous solution of epoxy-activated HA into a film. It is inherent in the method that all other components in the cross-linking step must be volatile.

WO 2004/092223 discloses a method of producing a cross-linked HA gel by drying a mixture of HA and epoxide cross-linking agent without substantially removing the epoxide.

Similarly, WO 2011/109129 and WO 2011/109130 discloses a process of producing HA threads by drying HA in the presence of a cross-linking agent under non-denaturing conditions.

U.S. Pat. No. 5,827,937 discloses a process for preparing polysaccharides having a high degree of cross-linking.

WO 00/046253 discloses a method involving two types of cross-linking steps, each in the presence of a cross-linking agent, for increasing the degree of cross-linking of HA.

US 2007/0066816 discloses a process for preparing double-cross-linked HA, involving cross-linking of a HA substrate in two steps with an epoxide and a carbodiimide, respectively.

U.S. Pat. No. 6,852,255 discloses a method involving cross-linking a water solution of HA followed by shaping of the cross-linked HA, e.g. by the addition of an organic solvent to precipitate the cross-linked HA.

U.S. Pat. No. 4,716,224 relates to a method for producing cross-linked HA having increased resistance to enzymatic decomposition. It is mentioned that HA may be precipitated prior to addition of the cross-linking agent.

KR 2007/0004159 discloses a method of preparing cross-linked HA by subjecting HA in solid phase to a cross-linking agent in an organic solvent.

EP 2 199 308 relates to a method of producing cross-linked HA by dispersing HA powder in aqueous alcohol prior to addition of a cross-linking agent.

U.S. Pat. No. 6,921,819 discloses a method for cross-linking HA in which a polyfunctional cross-linking agent is reacted with HA in the solid state during hydration thereof.

Despite these advances in the field, there remains a need for alternative methods of manufacturing cross-linked HA products having suitable liquid retention capacity and degradation profile, but with retained biocompatibility. In particular, it is desirable to minimize the degree of modification that is needed to obtain a HA gel product having a desired gel strength, which for instance can be measured as liquid retention capacity.

SUMMARY OF THE INVENTION

It is a purpose of the present invention to provide a novel process for manufacturing a cross-linked hyaluronic acid (HA) product, which meets one or more of the following requirements:

Low incorporation of cross-linking agent
Limited side reactions, e.g. with surrounding medium and halide ions
Controlled reaction conditions
Good process reproducibility
Suitable for scaling-up to an industrial process
Limited overall process time
Sufficient gel strength to resist deformation and migration when implanted
Allowing use of multiple types of agents (e.g. buffers, bases, acids, salts) in the process steps.

In order to achieve these goals and/or other goals that are evident from the present specification, it has been realized that it is an underlying object of the present invention to provide a process for manufacturing a cross-linked HA product having a low to moderate degree of modification while at the same time having a high gel strength as shown by low to moderate liquid retention capacity, or swelling degree.

The present invention provides versatile control of the HA cross-linking process by controlling the modification efficiency for a particular cross-linking agent with HA, i.e. controlling the efficiency of the cross-linking procedure in producing a gel of desired strength. The present invention therefore allows for manufacturing of a gel having a desired strength (a limited swelling degree) with a surprisingly low chemical modification of the HA. This is advantageous in order to minimize problems with biocompatibility, but generally also to improve control of the HA cross-linking process.

It is also an object of the present invention to provide a method for manufacturing a cross-linked HA product wherein a high proportion of the bound cross-linking agent(s) is connected in (at least) two ends, i.e. to achieve a high cross-linking efficiency.

It is a further object of the present invention to provide a cross-linked HA product having a low to moderate degree of modification and at the same time a low to moderate liquid retention capacity, or swelling degree.

It is an object of the present invention to provide a cross-linked HA product that has a high resistance against deformation.

For these and other objects that will be evident from this disclosure, the present invention provides according to a first aspect a process for manufacturing a cross-linked hyaluronic acid (HA) product, comprising (a) initiating cross-linking of HA by reacting HA with one or more polyfunctional cross-linking agents in an aqueous solution to obtain an activated HA; (b) removing unreacted cross-linking agent(s) from the activated HA; and (c) finalizing the cross-linking of the activated HA by subjecting the activated HA to further cross-linking conditions without addition of any additional cross-linking agent to obtain a cross-linked HA product; wherein the finalizing cross-linking step (c) is performed in a suspension of a liquid precipitating medium and the activated HA in precipitated form.

This process provides a good control of the final cross-linking step since it only occurs in solid (precipitated) phase. The resulting product is unique in that it is a gel with a low swelling degree despite the low degree of modification of the HA. It is highly surprising that a gel product having a limited swelling degree at all can be obtained with this low degree of modification.

In one embodiment of the process according to the invention, the removing step (b) comprises: (b1) precipitating the activated HA in a liquid precipitating medium to obtain a suspension comprising the liquid precipitating medium and the activated HA in precipitated form; and (b2) removing unreacted cross-linking agent(s) from the suspension of precipitated, activated HA. Optionally, the removing substep (b2) comprises washing the precipitated, activated HA with a liquid precipitating medium. The removal of cross-linking agent from activated HA in precipitated form is advantageous because it rapidly yields a very clean intermediate product, i.e. without remaining unreacted cross-linking agent. This cross-linking agent removal step is also very useful in a large-scale process.

In another embodiment of the process according to the invention, the finalizing cross-linking step (c) comprises: (c1) precipitating the activated HA in a liquid precipitating medium to obtain a suspension comprising the liquid precipitating medium and the activated HA in precipitated form; and (c2) finalizing the cross-linking of the activated HA by subjecting the suspension of precipitated, activated HA to further cross-linking conditions without addition of any additional cross-linking agent to obtain a cross-linked HA product.

In certain embodiments of the process according to the invention, the liquid precipitating medium contains more than 65 wt % of a water-soluble organic solvent, and preferably 70-80 wt % of a water-soluble organic solvent, and 20-30 wt % water.

In some embodiments of the process according to the invention, the water-soluble organic solvent is comprising or consisting of one or more lower alkyl alcohols, and preferably ethanol.

In specific embodiments of the process according to the invention, the initial cross-linking step (a) provides an activated HA in gel form. This gel form facilitates downstream steps, such as handling, shaping, washing and precipitating.

In certain embodiments of the process according to the invention, the cross-linking agent is selected from the group consisting of divinyl sulfone, multiepoxides and diepoxides. A preferred group of cross-linking agents is consisting of 1,4-butanediol diglycidyl ether (BDDE), 1,2-ethanediol diglycidyl ether (EDDE) and diepoxyoctane, and in particular 1,4-butanediol diglycidyl ether (BDDE).

In specific embodiments of the process according to the invention, the process is further comprising the steps of: (d) subjecting the precipitated, cross-linked HA product from step (c) to non-precipitating conditions; and (e) isolating the cross-linked HA product in non-precipitated form.

In some embodiments of the process according to the invention, the process is further comprising a step of sterilizing the cross-linked HA product.

The present invention provides according to a second aspect a cross-linked HA product having an effective cross-linker ratio of 0.35 or 35% or higher, and preferably in the range of 35-80%, such as 40-80% or 50-80%. The effective cross-linker ratio (CrR) describes the proportion of total bound cross-linking agent(s) (HA-X-HA and HA-X) that has bound two (or more) disaccharides (only HA-X-HA), where X is a cross-linking agent. The effective cross-linker ratio may for example be determined by LC-MS following enzymatic degradation of the HA gel. As an example, determination of the effective cross-linker ratio can be made by determination of HA-X fragments using LC-MS following enzymatic degradation of the HA gel, e.g. using chondroitinase AC from *Arthrobacter aurescens* or chondroitinase ABC from *Proteus vulgaris*, into fragments consisting of the main disaccharide (Δdi-HA) and fragments with bound cross-linking agent (HA-X) containing 1-8 disaccharides. The fragments can then be separated using size exclusion chromatography (SEC), and detected using mass spectrometry (MS). The method may readily be adapted for any polyfunctional cross-linking agent using the principles outlined in (Kenne et al., Carbohydrate Polymers 91 (2013) 410-418) and correcting/adapting the masses of the HA-X and HA-X-HA fragments in the LC-MS aquisition method for the specific cross-linking agent used.

In some embodiments of the cross-linked HA product according to the invention, the product has a swelling degree of 4-500 mL per g HA, and preferably 15-300 mL per g HA.

The present invention provides according to a third aspect an aqueous composition comprising a cross-linked HA product according to the invention, and optionally a buffering agent and/or a tonicity agent.

According to a fourth aspect, the present invention provides a pre-filled syringe, which is pre-filled with a cross-linked HA product according to the invention or an aqueous composition thereof.

The present invention provides according to a fifth aspect the use of a cross-linked HA product according to the invention or an aqueous composition thereof in cosmetic surgery, e.g. dermal filling, body contouring and facial contouring, in medical surgery, e.g. dermal filling, body contouring, prevention of tissue adhesion, formation of channels, incontinence treatment, and orthopaedic applications, and for hydrating and/or vitalizing the skin.

According to a sixth aspect, the present invention provides a method of treatment of a subject undergoing cosmetic or medical surgery, involving administration of a cross-linked HA product according to the invention, or an aqueous composition thereof, to a subject in need thereof.

BRIEF DESCRIPTION OF THE DRAWINGS

FIG. 2 shows schematic continuations of processes for cross-linking HA.

FIG. 3 shows effective cross-linker ratio (CrR) for HA particles for different reaction times and temperatures in the final cross-linking step.

FIG. 4 shows heat-induced degradation of cross-linked HA gels.

FIG. 5 shows peroxyl radical-induced degradation of cross-linked HA gels.

ITEMIZED LISTING OF EMBODIMENTS

Figure 1:
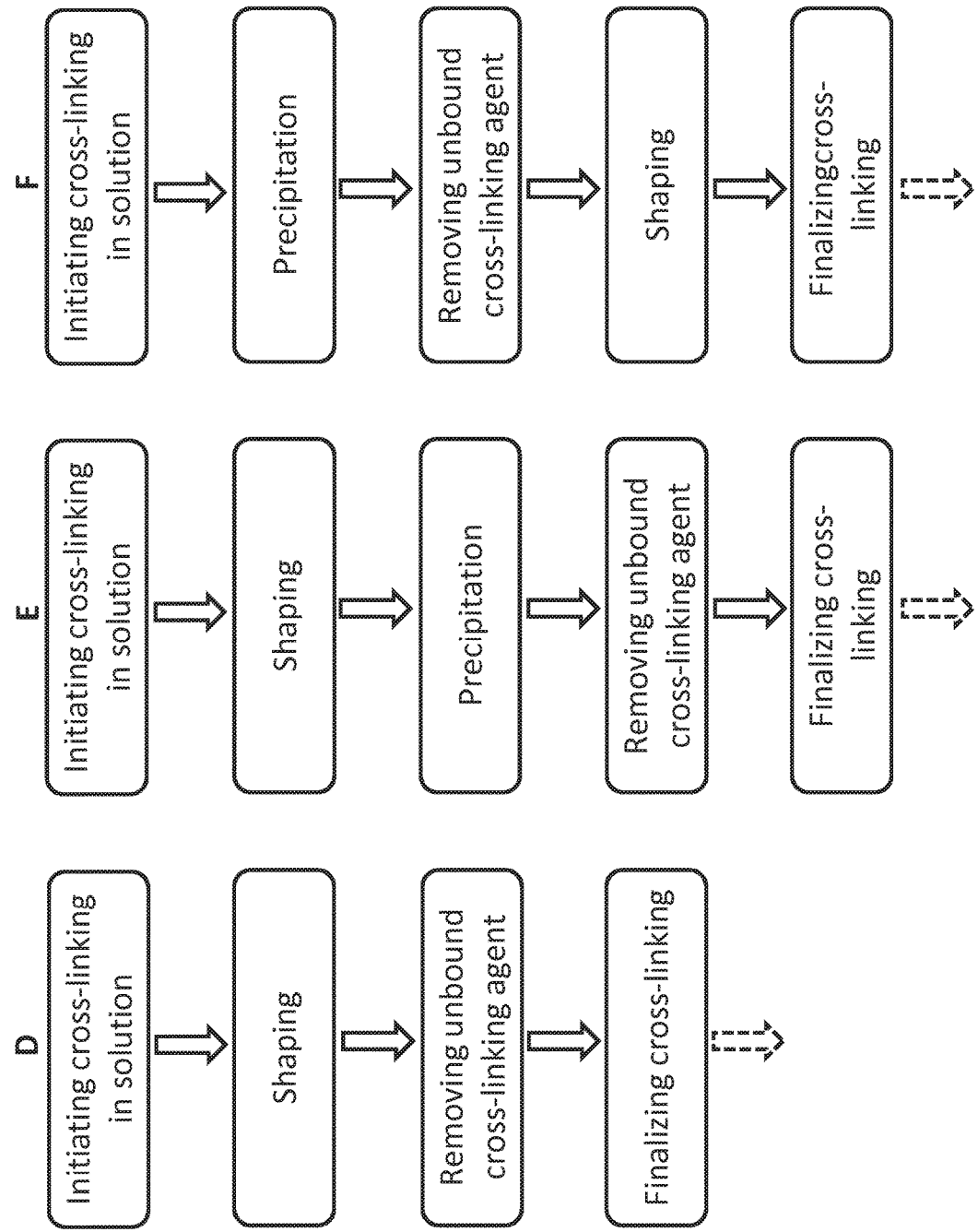
FIG. 1 shows schematic processes for cross-linking HA.

1. A process for manufacturing a cross-linked hyaluronic acid (HA) product, comprising
(a) initiating cross-linking of HA by reacting HA with one or more polyfunctional cross-linking agents in an aqueous solution to obtain an activated HA;
(b) removing unreacted cross-linking agent(s) from the activated HA; and
(c) finalizing the cross-linking of the activated HA by subjecting the activated HA to further cross-linking conditions without addition of any additional cross-linking agent to obtain a cross-linked HA product; wherein the finalizing cross-linking step (c) is performed in a suspension of a liquid precipitating medium and the activated HA in precipitated form.

2. A process according to embodiment 1, wherein the removing step
(b) comprises:
(b1) precipitating the activated HA in a liquid precipitating medium to obtain a suspension comprising the liquid precipitating medium and the activated HA in precipitated form; and
(b2) removing unreacted cross-linking agent(s) from the suspension of precipitated, activated HA.

3. A process according to embodiment 2, wherein the removing substep (b2) comprises washing the precipitated, activated HA with a liquid precipitating medium.

4. A process according to embodiment 1, wherein the finalizing cross-linking step (c) comprises:
(c1) precipitating the activated HA in a liquid precipitating medium to obtain a suspension comprising the liquid precipitating medium and the activated HA in precipitated form; and
(c2) finalizing the cross-linking of the activated HA by subjecting the suspension of precipitated, activated HA to further cross-linking conditions without addition of any additional cross-linking agent to obtain a cross-linked HA product.

5. A process according to any preceding embodiment, wherein the liquid precipitating medium contains more than 65 wt % of a water-soluble organic solvent.

6. A process according embodiment 5, wherein the liquid precipitating medium contains 70-80 wt % of a water-soluble organic solvent, and 20-30 wt % water.

7. A process according to any one of embodiments 5-6, wherein the water-soluble organic solvent is comprising one or more lower alkyl alcohols.

8. A process according to embodiment 7, wherein the water-soluble organic solvent is ethanol.

9. A process according to any preceding embodiment, wherein the suspension in the finalizing cross-linking step (c) has a pH of 9 or higher.

10. A process according to any preceding embodiment, wherein the finalizing cross-linking step (c) occurs at a temperature of 10-50° C.

11. A process according to any preceding embodiment, wherein the solution in the initial cross-linking step (a) has a pH of 9 or higher.

12. A process according to any preceding embodiment, wherein the initial cross-linking step (a) occurs at a temperature of 10-55° C.

13. A process according to any preceding embodiment, wherein the initial cross-linking step (a) provides an activated HA in gel form.

14. A process according to any preceding embodiment, comprising the preparation of a desired shape of the activated HA obtained in step (a) prior to the final cross-linking in step (c).

15. A process according to embodiment 14, wherein the preparation of a desired shape of the activated HA obtained in step (a) occurs prior to the removing of unreacted cross-linking agent(s) from the activated HA in step (b).

16. A process according to any one of embodiments 14-15, wherein the desired shape is particles having a size of 0.1-5.0 mm.

17. A process according to any one of embodiments 14-15, wherein the desired shape is a string, a net, or a film.

18. A process according to embodiment 17, wherein the desired shape is a string, said string having a ratio between its length and its width of 5:1 or higher.

19. A process according to any preceding embodiment, wherein the cross-linking agent is selected from the group consisting of divinyl sulfone, multiepoxides and diepoxides.

20. A process according to embodiment 19, wherein the cross-linking agent is selected from the group consisting of 1,4-butanediol diglycidyl ether (BDDE), 1,2-ethanediol diglycidyl ether (EDDE) and diepoxyoctane.

21. A process according to embodiment 20, wherein the cross-linking agent is 1,4-butanediol diglycidyl ether (BDDE).

22. A process according to any preceding embodiment, further comprising the steps of:
(d) subjecting the precipitated, cross-linked HA product from step (c) to non-precipitating conditions; and
(e) isolating the cross-linked HA product in non-precipitated form.

23. A process according to any preceding embodiment, comprising a step of sterilizing the cross-linked HA product.

24. A cross-linked HA product having an effective cross-linker ratio of 35% or higher.

25. A cross-linked HA product according to embodiment 24, having an effective cross-linker ratio in the range of 35-80%.

26. A cross-linked HA product according to any one of embodiments 24-25, having a swelling degree of 4-500 mL per g HA.

27. A cross-linked HA product according to embodiment 26, having a swelling degree of 15-300 mL per g HA.

28. A cross-linked HA product prepared by the process according to any one of embodiments 1-23.

29. A cross-linked HA product according to any one of embodiments 24-27, prepared by the process according to any one of embodiments 1-23.

30. A cross-linked HA product according to any one of embodiments 24-29, wherein the HA product has the shape of particles having a size of 0.1-5.0 mm.

31. A cross-linked HA product according to any one of embodiments 24-29, wherein the HA product has the shape of a string, a net, or a film.

32. A cross-linked HA product according to embodiment 31, wherein the shape is a string, said string having a ratio between its length and its width of 5:1 or higher.

33. A cross-linked HA product according to any one of embodiments 24-32, wherein the HA product is in dried form.

34. An aqueous composition comprising a cross-linked HA product according to any one of embodiments 24-32, and optionally a buffering agent and/or a tonicity agent.

35. An aqueous composition according to embodiment 34, further comprising one or more medical compound(s).

36. An aqueous composition according to embodiment 35, said medical compound(s) being selected from the group consisting of local anaesthetics anti-inflammatory drugs, antibiotics, and bone growth factors.

37. An aqueous composition according to embodiment 36, said medical compound(s) including lidocaine hydrochloride.

38. Use of a cross-linked HA product according to any one of embodiments 24-33 or an aqueous composition according to any one of embodiments 34-37 in cosmetic surgery, such as dermal filling, body contouring and facial contouring.

39. Use according to embodiment 38, wherein the cosmetic surgery is facial contouring.

40. Use of a cross-linked HA product according to any one of embodiments 24-33 or an aqueous composition according to any one of embodiments 34-37 for hydrating and/or vitalizing the skin.

41. A cross-linked HA product according to any one of embodiments 24-33 or an aqueous composition according to any one of embodiments 34-37 for use as a medicament or medical device.

42. A cross-linked HA product according to any one of embodiments 24-33 or an aqueous composition according to any one of embodiments 34-37 for use in cosmetic surgery, such as dermal filling, body contouring and facial contouring, or medical surgery such as dermal filling, body contouring, prevention of tissue adhesion, formation of channels, incontinence treatment, and orthopaedic applications.

43. A cross-linked HA product according to embodiment 42, wherein the cosmetic surgery is facial contouring.

44. Use of a cross-linked HA product according to any one of embodiments 24-33 or an aqueous composition according to any one of embodiments 34-37 in the manufacture of a medicament or a medical device for use in cosmetic surgery, such as dermal filling, body contouring and facial contouring, or medical surgery such as dermal filling, body contouring, prevention of tissue adhesion, formation of channels, incontinence treatment, and orthopaedic applications.

45. Use according to embodiment 44, wherein the cosmetic surgery is facial contouring.

46. A pre-filled syringe, which is pre-filled with a cross-linked HA product according to any one of embodiments 24-33 or an aqueous composition according to any one of embodiments 34-37.

47. A method of treatment of a subject undergoing cosmetic or medical surgery, involving administration of a cross-linked HA product according to any one of embodiments 24-33 or an aqueous composition according to any one of embodiments 34-37 to a subject in need thereof.

48. A method according to embodiment 47, wherein the cosmetic surgery is facial contouring.

DETAILED DESCRIPTION OF THE INVENTION

The present invention provides according to a first aspect a process for manufacturing a cross-linked hyaluronic acid (HA) product, which exhibits highly desirable properties. This process provides a good control of the final cross-linking step since it only occurs in solid (precipitated) phase. The resulting product is unique in that it is a gel with a low swelling degree despite the low degree of modification of the HA. It is highly surprising that a gel product having a limited swelling degree at all can be obtained with this low degree of modification. Among many applications, this process allows for manufacturing of cross-linked HA products having a predefined shape that is retained during the manufacturing process. The process also allows for manufacturing of biocompatible shaped cross-linked HA products.

Unless otherwise provided, the terms "hyaluronic acid" and "HA" are used interchangeably and encompass all variants and combinations of variants of hyaluronic acid, or hyaluronan, of various chain lengths and charge states, as well as with various chemical modifications That is, the term also encompasses the various hyaluronate salts of HA, such as sodium hyaluronate (NaHA). Various modifications of the HA are also encompassed by the term, such as oxidation, e.g. oxidation of $CH_2OH$ groups to COOH; periodate oxidation of vicinal hydroxyl groups, optionally followed by reduction or imine formation etc; reduction, e.g. reduction of COOH to $CH_2OH$; sulphation; deamidation, optionally followed by deamination or amide formation with new acids; esterification; substitutions with various compounds, e.g. using a cross-linking agent or a carbodiimide; including coupling of different molecules, such as proteins, peptides and active drug components, to HA; and deacetylation. It is well known to the skilled person that the various forms of HA have different chemical properties that have to be taken into account during chemical modification and analysis. For instance, if it is desired to obtain a solution of HA having a certain pH, the acidity of the material to be dissolved, the acidity of the dissolving liquid and any buffering capacity will all affect the resulting pH of the solution.

It is preferred that the HA substrate is a HA or hyaluronate salt without chemical modifications, i.e. which has not been subjected to cross-linking or other modifications prior to the present manufacturing method.

The HA can be obtained from various sources of animal and non-animal origin. Sources of non-animal origin include yeast and preferably bacteria. The molecular weight of a single HA molecule is typically in the range of 1.5-3 MDa, but other ranges of molecular weights are possible, e.g. 0.5-10 MDa.

The product that is manufactured by the method is a cross-linked HA. The method provides cross-links between the HA chains, which creates a continuous shaped network of HA molecules which is held together by the covalent cross-links, physical entangling of the HA chains and various interactions, such as hydrogen bonding, van der Waals forces and electrostatic interactions. The cross-linked HA product according to the invention is a gel, or a hydrogel. That is, it can be regarded as a water-insoluble, but substantially dilute, cross-linked system of HA molecules when subjected to a liquid, typically an aqueous liquid.

The resulting cross-linked HA product is preferably biocompatible. This implies that no, or only very mild, immune response occurs in the treated individual.

Since cross-linked HA gel products are highly complex chemical structures, they are typically characterised by a combination of their chemical structures and their physical properties. The deviation in chemical structure from unmodified HA is typically reported as degree of modification, modification degree, cross-linking degree, cross-linking index or chemical modification, which all relate to the amount of cross-linking agent covalently bound to the HA. Throughout this text, the term degree of modification will be used.

The most relevant physical properties of the cross-linked HA gel product are the volume of liquid that the gel can absorb and the rheological properties of the gel. Both properties describe the structural stability of the gel, often referred to as gel strength or firmness, but while the absorption of liquid can be determined for a dry gel, the rheological properties have to be measured on a gel that is swollen to a desired concentration. Traditional expressions for the liquid absorption are swelling, swelling capacity, liquid retention capacity, swelling degree, degree of swelling, maximum liquid uptake and maximum swelling. Throughout this text, the term swelling degree will be used. Regarding the rheological properties of cross-linked HA gel products, it can be noted that rotational rheometry is only useful for determining the rheology of liquids, whereas oscillating rheometry is necessary to determine the rheology of gels. The measurement yields the resistance of the gel to deformation in terms of elastic modulus and viscous modulus. A high gel strength will give a large resistance to deformation of the gel product swollen to a desired concentration.

Some known soft-tissue augmentation treatments involving implants occasionally suffer from the drawback that the implant, or part thereof, migrates away from the desired site of treatment. In order to avoid this problem, the gel is required to have a certain gel strength in order to resist deformation. This property can be measured using rheometry in the oscillating mode.

The process according to the invention is comprising, and optionally consisting of, at least three steps: an initial, or initiating, cross-linking step, a cross-linking agent removal step, and a final, or finalizing, cross-linking step. The first cross-linking step can be performed using many different temperatures, times and concentrations. It is in the first cross-linking step that the degree of modification is determined and a smaller part of the cross-linking occurs. Independently of how the first cross-linking is performed, the effective cross-linker ratio is increased during the second cross-linking step, typically by a factor of 2-6, or even higher.

In the first process step, cross-linking of a HA substrate is initiated, or expressed in another way, initial cross-linking of the HA substrate is performed. The HA substrate is present in an aqueous solution and is allowed to react with one or more polyfunctional cross-linking agents. This results in a substantial cross-linking of the HA substrate, i.e. covalent coupling of two separate HA molecules or two distant parts of the same HA molecule is achieved already in this step. As will be evident from the disclosure of the other process steps, cross-linking agent is only added prior to or during this initial cross-linking step.

In a preferred embodiment, the initial cross-linking step provides an activated HA in gel form. In addition to these cross-links between separate HA molecules or distant parts of the same HA molecule, this also results in numerous cross-linking agents being covalently coupled to the HA substrate in a single position, and that the HA resulting from this step is substituted with several cross-linking agents exhibiting reactive cross-linking functions. The resulting activated HA thus contains a mixture of cross-linked HA molecules, wherein each cross-link involves a covalent coupling between (at least) two separate HA molecules or two distant parts of the same HA molecule, and HA substituted with cross-linking agents exhibiting reactive cross-linking functions, i.e. typically involving single covalent coupling of the still reactive cross-linking agent to the HA.

The HA substrate is dissolved in the aqueous solution. By the terms "dissolved" and "solution" is understood that the HA substrate is present in a homogeneous mixture with a liquid, in which mixture energetically favourable interactions occur. Addition of liquid to the solution lowers the concentration of the dissolved HA substrate. The solution is aqueous, i.e. it contains water. The aqueous solution may simply consist of the HA substrate dissolved in water. In a preferred embodiment, the solution in the initial cross-linking step has a pH of 9 or higher, such as 10 or higher, or even 11 and higher.

In general terms, the initial cross-linking step can be made using any concentrations of HA and cross-linking agent, and the time and temperature can vary, as long as an initial cross-linking of HA is achieved and there are remaining reactive cross-linking agents covalently attached to the HA.

The initial cross-linking step is typically carried out at a temperature of 10-75° C., but it is preferred that the step is carried out at room temperature, e.g. 20-25° C. Other preferred temperature ranges are 10-55° C., such as 18-35° C. and 35-55° C.

The aqueous solution of the initial cross-linking step contains one or more cross-linking agent(s) that is polyfunctional, i.e. that has two or more reaction sites for forming covalent bonds to the HA molecules that are being cross-linked. It is preferred that the cross-linking agent(s) that is used in this third step is bifunctional, i.e. it has two reaction sites for forming covalent bonds to the HA molecules that are being cross-linked. Without being limited thereto, useful polyfunctional cross-linking agents include divinyl sulfone, multiepoxides and diepoxides, such as 1,4-butanediol diglycidyl ether (BDDE), 1,2-ethanediol diglycidyl ether (EDDE) and diepoxyoctane, preferably BDDE. It is desirable that the one or more polyfunctional cross-linking agent(s) provides ether cross-links.

The initial cross-linking step may also involve, or be followed by, the preparation of a desired shape of the activated HA obtained, such as a particle, a fibre, a string, a strand, a net, a film, a disc and a bead. This may be accomplished in various ways, e.g. extrusion, mincing and moulding. Extrusion of the HA substrate typically involves pressing it through an opening of desired size. The dimensions, e.g. the thickness, of the fibre, string or strand can be controlled by varying the dimension or type of opening, e.g. using various opening diameters in the range of 0.1-2 mm or 14-30 G, the extrusion pressure, the extrusion speed and/or the HA concentration. By using other types of orifices and chinks, different shapes or structures can be produced. In the alternative, particles or beads of desired sizes can be prepared by mincing a gel of activated HA, e.g. by pressing the activated HA through a mesh material having desired mesh (opening) size. The HA can also be moulded in various forms, e.g. as a film, a net, discs or beads.

This shape can be maintained throughout the manufacturing process and in the final product. It is preferred that the shape has an extension of less than 5 mm, preferably less than 1 mm, and larger than 0.5 mm or even larger than 0.8 mm when the HA substrate is in swollen form in physiological saline. A preferred shape is particles or beads having a size of 0.1-5.0 mm, such as 0.5-1 mm, when fully swollen in physiological saline. In the cases of fibres, strings, strands, nets and films, considerably larger dimensions than 5 mm in one or two dimensions, respectively, may be applicable.

The initial cross-linking and optional shaping is followed by a cross-linking agent removal step. This step involves removing unreacted cross-linking agent(s) from the activated HA. As set out above, the activated HA resulting from the initial cross-linking step contains a mixture of cross-linked HA molecules and HA substituted with cross-linking agents exhibiting reactive cross-linking functions. Following the initial cross-linking step, there is also a significant presence of cross-linking agent which is not covalently coupled to HA, either because it has not reacted at all or because it has reacted with water molecules or with other components of the aqueous medium, e.g. chloride ions. The unreacted cross-linking agent, i.e. cross-linking agent which is not covalently coupled to HA, is removed in this step by any suitable means, such as dialysis and washing, involving e.g. filtration, decanting and/or centrifugation. It goes without saying that no cross-linking agent(s) is added in this step.

In a preferred embodiment, the activated HA which is associated with unreacted cross-linking agent(s) is precipitated in a liquid precipitating medium prior to or at the same time as the unreacted cross-linking agent(s) is removed.

The activated HA is precipitated due to reduction of the solubility of the HA. This is typically achieved by subjecting the activated HA to a liquid medium in which it is insoluble. As the skilled person is well aware, this may be achieved by adding the activated HA to the precipitating medium, by adding the precipitating medium to the activated HA, or by other suitable method steps. The liquid precipitating medium comprises an amount of one or more water-soluble organic solvent(s) giving precipitating conditions for HA. The resulting solid HA precipitate falls out of the solute phase and can typically be separated from the remaining liquid by filtration, decanting, centrifugation, or manually using a pair of tweezers or the like. The resulting suspension is comprising the liquid precipitating medium and the activated HA in precipitated form. The unreacted cross-linking agent(s) is washed away by any suitable means, such as dialysis and washing, involving e.g. filtration, decanting and/or centrifugation. It is preferred that the unreacted cross-linking agent(s) is removed from the suspension of precipitated, activated HA by washing the precipitated, activated HA with a liquid precipitating medium, typically the same type of liquid precipitating medium used for precipitating the activated HA. The removal of cross-linking agent from activated HA in precipitated form is advantageous because it rapidly yields a very clean intermediate product, i.e. without remaining unreacted cross-linking agent. This cross-linking agent removal step is also very useful in a large-scale process.

Depending on the liquid medium in which it is present, HA or HA gel can be in dissolved or swelled gel form or in precipitated form.

In a good HA solvent, i.e. in a solvent where interactions between HA and solvent are energetically favored over interactions between the HA molecules themselves, the HA or HA gel will be in dissolved or swelled gel form. One example of a good HA solvent is water.

In a poor HA solvent or HA non-solvent, i.e. in a solvent where interactions between the HA molecules themselves are energetically favored over interactions between HA and solvent, the HA or HA gel will be in precipitated form. One example of a poor HA solvent is ethanol.

The term "liquid precipitating medium", as used herein, refers to a liquid medium in which the activated HA will be in precipitate when immersed. In other words, the liquid precipitating medium is a non-solvent for the activated HA.

The liquid precipitating medium typically contains more than 50 wt %, such as more than 65 wt % of a water-soluble organic solvent, dissolved in water and optional further constituents, such as salts, buffers, bases and acids. The water-soluble organic solvent shall be present in a concentration that is sufficient to achieve precipitation of the activated HA, but not necessarily in excessive amounts. In preferred embodiments, the liquid precipitating medium is comprising, or contains, more than 50 wt % of a water-soluble organic solvent, and up to 50 wt % water, and preferably 60-90 wt % or 65-85 wt % of a water-soluble organic solvent, and 10-40 wt % or 15-35 wt % water. In specific embodiments, the liquid precipitating medium is comprising more than 60 wt %, preferably 60-90 wt % or 65-85 wt %, of a water-soluble organic solvent, further constituents, such as salts, buffers, bases and acids, and water to a total of 100 wt %.

The organic solvents that are used according to the invention are carbon-containing solvents and may exhibit a varying degree of polarity. Although termed "solvents", it shall be understood that these organic solvents are utilized for balancing and shifting the solubility of HA during the manufacturing process. The HA may very well be dissolved in an organic solvent at a certain organic solvent concentration interval, but falls out and forms a precipitate when the organic solvent concentration is increased. For instance, HA can be dissolved in a 50/50 (wt/wt) mixture of an organic solvent, e.g. a lower alkyl alcohol, and water, but falls out and forms a precipitate in a 90/10 (wt/wt) mixture. When subjected to non-precipitating conditions, e.g. a 50/50 or a 0/100 mixture, the HA returns to the non-precipitated, dissolved state. The skilled person is well aware that other factors may have an impact on the limiting organic solvent(s) concentration for precipitation of HA, such as temperature, pH, ion strength and type of organic solvent(s). The limiting concentration for precipitation of HA under given conditions is well known or can easily be determined by a skilled person in the field. By way of example, the limiting concentration for precipitation of HA (in mixture of water and ethanol) is approximately 65 wt % ethanol.

Without being limited thereto, the organic solvents according to the invention can be selected from the group consisting of pentane, hexane, cyclohexane, 1,4-dioxane, N,N-dimethylformamide, N,N-dimethylacetamide, ethyl acetate, acetamide, diethyl ether, tetrahydrofurane, acetonitrile, methyl ethyl ketone, acetone, lower alkyl alcohols, e.g. methanol, ethanol, propanol, isopropanol and butanol. The organic solvents according to the invention are water-soluble. A preferred group of organic solvents is the lower alkyl alcohols. The term lower alkyl alcohol includes primary, secondary and tertiary alkyl alcohols having from one to six carbon atoms, i.e. $C_{1-6}$ alkyl alcohols. Specific examples of lower alkyl alcohols include methanol, ethanol, denatured spirit, n-propanol, isopropanol, n-butanol, isobutanol, and t-butanol. Preferred lower alkyl alcohols are methanol and ethanol, in particular ethanol, due to price, availability and easy handling.

The cross-linking agent removal step may also involve, or be followed by, the preparation of a desired shape of the activated HA obtained, such as a particle, a fibre, a string, a strand, a net, a film, a disc and a bead. It is preferred that the preparation of a desired shape of the activated HA occurs prior to the actual removing of unreacted cross-linking agent(s) from the activated HA in step. Thus, the preparation of a desired shape may preferably occur prior to any precipitation of the activated HA.

The preparation of a desired shape may be accomplished in various ways, e.g. extrusion, mincing and moulding. Extrusion of the HA substrate typically involves pressing it through an opening of desired size. The dimensions, e.g. the thickness, of the fibre, string or strand can be controlled by varying the dimension or type of opening, e.g. using various opening diameters in the range of 0.1-2 mm or 14-30 G, the extrusion pressure, the extrusion speed and/or the HA concentration. By using other types of orifices and chinks, different shapes or structures can be produced. In the alternative, particles or beads of desired sizes can be prepared by mincing a gel of activated HA, e.g. by pressing the activated HA through a mesh material having desired mesh (opening) size. The HA can also be moulded in various forms, e.g. as a film, a net, discs or beads.

This shape can be maintained throughout the manufacturing process and in the final product. In certain preferred embodiments, the shape has an extension of less than 5 mm, preferably less than 1 mm, and larger than 0.5 mm or even larger than 0.8 mm when the HA substrate is in swollen form in physiological saline. A preferred shape is particles or beads having a size of 0.1-5.0 mm, such as 0.2-3.0 mm or 0.5-1 mm, when fully swollen in physiological saline. In certain other preferred embodiments, the shape has an extension of more, or considerably more, than 5 mm in at least one dimension when the HA substrate is in swollen form in physiological saline. A preferred shape is fibres, strings or strands having a length of several centimeters, e.g. 1-100 centimeters. It is preferred that the ratio between its length and its width or its average diameter is 5:1 or higher, such as 100:1 or higher, and optionally 10 000:1 or lower, such as 2500:1 or lower.

The cross-linking agent removal and optional shaping is followed by a final, or finalizing, cross-linking step. In this process step, cross-linking of activated HA substrate is finalized. The remaining reactive groups in the cross-linking agents which have been covalently attached to the HA in the initial cross-linking step are reacted with further available sites on the activated HA to achieve further cross-links, i.e. covalent couplings between (at least) two separate HA molecules or two distant parts of the same HA molecule. It is preferable that a desired shape of the activated HA obtained in the initial cross-linking step is prepared prior to this finalizing cross-linking step.

Although this step finalizes the cross-linking of the HA, it shall be noted that no free, or unbound, cross-linking agent is present in this step. Any remaining unbound cross-linking agent(s) from the initial cross-linking step has been removed in the cross-linking agent removal step. It follows that cross-linking agent shall not be added in this step, or in any step subsequent to the initial cross-linking step or the cross-linking agent removal step. Although the final cross-linked HA product may be processed into different shapes, it is preferred that the activated HA has been processed into a desired shape prior to the final cross-linking step.

The cross-linking of the activated HA into a cross-linked HA product is finalized by subjecting the activated HA to further cross-linking conditions. The finalizing cross-linking step is performed in a suspension of a liquid precipitating medium and the activated HA in precipitated form. It is believed that this improves the effective cross-linker ratio (CrR), i.e. the proportion of total bound cross-linking agent(s) (HA-X-HA and HA-X) that has bound two (or more) disaccharides (only HA-X-HA). Without desiring to be bound by any particular theory, this may be due firstly to that the HA chains are brought closer to each other and secondly to the local absence of competing water molecules within in the precipitated HA network. Performing the finalizing cross-linking step in a suspension of the activated HA in precipitated form also limits the side reactions, e.g. with the surrounding precipitating medium and halide ions. No additional cross-linking agent is added in this step.

Finalizing cross-linking means the cross-linking that will occur upon introduction of cross-linking conditions in the suspension of the activated HA in precipitated form. Cross-linking conditions means conditions under which cross-linking agents exhibiting reactive functions will react with available sites on the activated HA to achieve further cross-links.

The term final or finalizing is used to distinguish the second cross-linking step from the first, initiating, cross-linking step. The finalizing cross-linking increases the proportion of total bound cross-linking agent(s) (HA-X-HA and HA-X) that has bound two (or more) disaccharides (only HA-X-HA).

As set out above, the activated HA may be precipitated in a liquid precipitating medium prior to or at the same time as the unreacted cross-linking agent(s) is removed. In the alternative, precipitation of the activated HA in a liquid precipitating medium is performed after the removal of unreacted cross-linking agent, e.g. prior to subjecting the activated HA to further cross-linking conditions in the final cross-linking step. Thus, the final cross-linking step may involve precipitating the activated HA in a liquid precipitating medium to obtain a suspension comprising the liquid precipitating medium and the activated HA in precipitated form; and finalizing the cross-linking of the activated HA by subjecting the suspension of precipitated, activated HA to further cross-linking conditions. Again, no additional cross-linking agent is added in this step.

In a preferred embodiment, the suspension in the finalizing cross-linking step has a pH of 9 or higher, such as 10 or higher, 11 or higher, or even 12 and higher.

The finalizing cross-linking step is typically carried out at a temperature of 10-75° C., but it is preferred that the step is carried out at room temperature, e.g. 20-25° C. Preferred temperature ranges are 10-50° C., such as 18-40° C.

The process according to the invention may also comprise one or more further steps. A preferred process step involves subjecting the precipitated, cross-linked HA product from the finalizing cross-linking step to non-precipitating conditions. This typically involves subjecting the cross-linked HA product to a liquid medium and allowing it to return to non-precipitated state. The liquid medium is typically water, saline or mixtures and/or combinations thereof, optionally with non-precipitating concentrations of an organic solvent, e.g. methanol or ethanol.

Due to the cross-linking, the resulting HA product is a continuous network of interconnected and entangled HA chains which under non-precipitating conditions absorbs liquid (swells) and forms a gel. The swelling can be allowed to proceed until the gel is fully swollen and no further liquid can be absorbed, or it can be interrupted at an earlier stage to obtain a partially swollen gel. A partially swollen gel can be useful as an intermediate for further processing of the gel, for instance further mechanical production of gel structures of a desired size and shape can be performed. By way of example, a film can be cut into particles, slices or pieces, gel fibres can be cut into shorter fragments, well defined irregular shapes can be designed from a film, etc. The cross-linked HA fibres, strings or strands can also be woven together to form a net or a film after completed cross-linking, before or after drying. It may also be convenient to use a partially swollen shaped gel product during implantation thereof at a desired site to facilitate administration and minimize patient discomfort and to enhance the lifting capacity by use of the remaining swelling capacity.

When the shaped gel product is subjected to non-precipitating conditions in an excess of liquid, it is also possible to determine its maximum swelling degree (SwD), or inversely its minimum HA concentration ($C_{min}$), i.e. the HA concentration when the gel product is fully swollen. Using the manufacturing method according to the invention, it is possible to obtain a swelling degree of 4-500 mL per g HA, and preferably 15-300 mL per g HA. This implies $C_{min}$ values in the range of 0.2-25% (w/w), i.e. 2-250 mg/g, such as 0.3-7% (w/w), i.e. 3-70 mg/g. It is preferred that the $C_{min}$ value is 0.3-5% (w/v), i.e. 3-50 mg/mL. It is highly advantageous that the desired swelling degree (or $C_{min}$ value) can be achieved with a minimal degree of modification, but the traditional way of regulating the swelling degree is by means of varying the degree of modification. The present manufacturing process therefore provides a new concept for regulating the swelling capacity of a shaped gel product, which surprisingly enables production of firm shaped gels with a high $C_{min}$ value (low swelling degree) in relation to the low degree of modification of the gel.

The modification efficiency (MoE) is a measure of the ratio between the minimum HA concentration ($C_{min}$), or rigidity/strength, of a gel and its degree of chemical modification (MoD) by cross-linking agent(s). Using the manufacturing method according to the present invention, it is possible to obtain a cross-linked HA product having a modification efficiency of 2 or higher, preferably in the range of 3-500, such as 5-200 or 7-100. Without desiring to be limited to any specific theory, it is contemplated that the beneficial properties of the gel are the result of a surprisingly high degree of effective cross-linking, i.e. a high degree of the bound cross-linking agent(s) (effective cross-linker ratio, typically 35% or higher, such as 40% or higher or even 50% or higher) is in fact bound to the HA at two (or more) sites, in combination with effective positioning of the cross-links for the desired purpose, and probably an extremely high degree of retained entanglement. In contrast to what a skilled person would expect from the low degree of modification of the resulting HA product, the method according to the invention surprisingly provides a gel with high rigidity/strength. Under any circumstances, the method according to the invention provides a useful way of further regulating the swelling degree in relation to the degree of modification.

Optionally, the manufacturing process also involves a step of isolating the cross-linked HA product. Depending on whether the product is held under precipitating conditions or has been subjected to non-precipitating conditions, this step may involve isolating the product in precipitated form or in non-precipitated form. The isolated, precipitated or non-precipitated, product can then be subjected to sterilizing, e.g. autoclaving, radiation, heating etc., so as to obtain a sterile cross-linked HA product.

If desired, other substances, such as local anaesthetics (e.g. lidocaine hydrochloride) anti-inflammatory drugs, antibiotics and other suitable supportive medications, e.g. bone growth factors or cells, may be added after the cross-linked HA product has been obtained.

Now referring to the figures, some preferred processes for manufacturing a cross-linked HA product are schematically illustrated in FIGS. 1-2. Each combination (1A-1F) of process steps shown in FIG. 1 provides a cross-linked HA product, but any of these may also be combined with any combination of further downstream process steps as illustrated by the dotted arrows and exemplified in FIG. 2 (2A-2D).

The most general process is illustrated in FIG. 1A, wherein cross-linking of HA is initiated by reacting HA with a polyfunctional cross-linking agent in an aqueous solution to obtain an activated HA. Any unreacted cross-linking agent is removed from the activated HA. The cross-linking of the activated HA is finalized by subjecting the activated HA in precipitated form to further cross-linking conditions in a suspension of a liquid precipitating medium, without addition of any additional cross-linking agent. These steps provide a cross-linked HA product according to the invention, having a low to moderate degree of modification while at the same time having a high gel strength as shown by low to moderate liquid retention capacity, or swelling degree.

As illustrated in FIGS. 1B-1C and 1E-1F, the precipitation of the activated HA may occur at any time between the initial cross-linking in solution and the finalizing cross-linking. The precipitation of the activated HA may thus occur prior to the removal of unbound cross-linking agent (FIGS. 1B, 1E-1F) or after the removal of unbound cross-linking agent (FIG. 1C).

The process according to the invention may also involve shaping of the activated HA, as illustrated in FIGS. 1D-1F. The shaping may occur at any time between the initial cross-linking in solution and the finalizing cross-linking. The shaping may thus occur prior to the removal of unbound cross-linking agent (FIGS. 1D, 1F) or after the removal of unbound cross-linking agent (FIG. 1F). The shaping may also occur prior to precipitation of the activated HA (FIG. 1E) or after precipitation of the activated HA (FIG. 1F).

The cross-linked HA product may also be subjected to further down-stream process steps, e.g. reswelling under non-precipitating conditions and/or isolating and/or sterilizing the product. For instance, the cross-linked HA product may be subjected to non-precipitating conditions and isolated from the production media, as set out in FIG. 2A.

The cross-linked HA product may also be subjected to sterilizing, e.g. autoclaving, as illustrated in FIGS. 2B-2D. For many applications, it is preferable that a ready-to-use device, such as an injector, is loaded with the cross-linked HA product, as illustrated in FIGS. 2C-2D. The HA product may be sterilized, e.g. autoclaved, prior to being loaded into the device (FIG. 2D), or after being loaded into the device (FIG. 2C).

According to one aspect, the invention provides a cross-linked HA product. According to one embodiment, the product is manufactured, or can be manufactured, by the manufacturing process of the invention. The cross-linked HA product according to the invention is a gel, or a hydrogel. That is, it can be regarded as a water-insoluble, but substantially dilute cross-linked system of HA molecules when subjected to a liquid, typically an aqueous liquid. The gel is mostly liquid by weight and can e.g. contain 90-99.9% water, but it behaves like a solid due to a three-dimensional cross-linked HA network within the liquid. Due to its significant liquid content, the shaped gel is structurally flexible and similar to natural tissue, which makes it very useful as a scaffold in tissue engineering and for tissue augmentation. It is the cross-links and their attachment positions at the HA molecules that, together with the natural entanglement of the HA chains, give the gel its structure and properties, which are intimately related to its swelling degree.

The amount of attached cross-linking agent(s) can be quantified by and reported as the degree of modification (MoD), i.e. the molar amount of bound cross-linking agent(s) relative to the total number of repeating HA disaccharide units. It is preferred that the cross-linked hyaluronic acid product according to the invention has a degree of modification of 1-90 cross-linking agent units per 1000 disaccharide units (0.1-9%), preferably 1-40 cross-linking agent units per 1000 disaccharide units (0.1-4%). The effectiveness of the cross-linking reaction is shown by the amount of attached cross-linking agent(s) that is connected in (at least) two ends to one (or more) HA chains and is reported as the effective cross-linker ratio (CrR). It has now surprisingly been realized and experimentally shown that the CrR advantageously can be manifold increased by dividing the cross-linking reactions into two separate steps, and in particular by including a HA precipitation step prior to the final cross-linking step. Specifically, the CrR is increased at least 1.5 times, and preferably 2-10, e.g. 2-6, times by the final cross-linking step. It is preferable that the product according to the invention has an effective cross-linker ratio of 35% or higher, more preferably 40% or higher, such as in the range of 40-80%, or even 50-80%. These products consequently have a low number of cross-linking agents that do not provide effective cross-links in the product. The high effective cross-linker ratios allow for a surprisingly low total degree of modification in relation to the gel strength, which in turn is advantageous to ensure high biocompatibility.

Another characteristic of a gel is its capacity to absorb water until it is fully swollen. Further addition of liquid will not dilute the gel further, i.e. the gel cannot be indefinitely diluted like a solution of free molecules. When the gel is subjected to non-precipitating conditions, it is also possible to determine its swelling degree, or inversely its minimum concentration ($C_{min}$), i.e. the HA concentration when the gel product is fully swollen. Harder (low-swelling) gels are generally less viscous, more elastic and expected to have a longer half-life in vivo than softer (high-swelling) gels. However, harder gels may be recognised as foreign materials by the body if they are highly chemically modified. It is preferred that the product according to the invention has a swelling degree of 4-500 mL per g HA, and preferably 15-300 mL per g HA. This implies $C_{min}$ values in the range of 0.2-25% (w/w), i.e. 2-250 mg/g, such as 0.3-7% (w/w), i.e. 3-70 mg/g. It is preferred that the $C_{min}$ value is 0.3-5% (w/v), i.e. 3-50 mg/mL.

The cross-linked HA product according to the inventions is cross-linked with one or more cross-linking agent(s) that is polyfunctional, i.e. it has two or more reaction sites for forming covalent bonds to the HA molecules that are being cross-linked. It is preferred that the cross-linking agent(s) is bifunctional, i.e. it has two reaction sites for forming covalent bonds to the HA molecules that are being cross-linked. Without being limited thereto, useful polyfunctional cross-linking agents include divinyl sulfone, multiepoxides and diepoxides, such as 1,4-butanediol diglycidyl ether (BDDE), 1,2-ethanediol diglycidyl ether (EDDE) and diepoxyoctane, preferably BDDE. It is desirable that the HA gel product is cross-linked with ether cross-links, which provide suitable stability.

The shaped HA gel product can be multiple cross-linked, i.e. containing at least two different types of bonds, preferably including ether bonds. It is preferred that the HA product is single cross-linked, i.e. containing essentially a single type of cross-links, preferably ether cross-links. A single cross-linked product has the advantage of being chemically well defined. It is advantageous that a product with a single type of cross-links displays such desirable properties. In specific embodiments, the HA product is cross-linked with ether cross-links, which provides a stable and autoclavable product.

It is highly advantageous that the desired swelling degree (or $C_{min}$ value) of the product is obtained with a minimal degree of modification, although the traditional way of regulating the swelling degree is by means of varying the degree of modification. The main reason for minimizing the degree of modification is to ensure that the biocompatibility of the gel is high, but the skilled person is well aware of other advantages. The shaped product is characterised by a high $C_{min}$ value (low swelling degree) in relation to the degree of modification of the gel. The modification efficiency (MoE) is a measure of the ratio between the minimum HA concentration ($C_{min}$), that reflects the rigidity and the strength of a gel, and the degree of chemical modification of the gel with cross-linking agent(s). The cross-linked HA product according to the invention has a modification efficiency of 2 or higher, preferably in the range of 3-500, such as in the range of 5-200 or 7-100. Products with a modification efficiency of 10 or higher, such as in the range of 20-190, combine for the first time a low to moderate degree of modification and at the same time a low to moderate swelling degree, or liquid retention capacity. Thereby, it is possible to provide a firm, cross-linked HA product that is biocompatible and that has a high resistance to deformation.

Furthermore, it is preferable that the cross-linked HA gel products according to the invention are viscoelastic. This implies that the gel products exhibit a combination of viscous and elastic properties. As is well known by the skilled person, the viscoelastic properties can be determined with a rheometer. In oscillating mode, the elastic modulus (G') and the viscous modulus (G") can be determined at a frequency of 0.1 or 1 Hz. For certain viscoelastic gel products according to the invention, it is preferred that the following relationship is satisfied:

$$0.1 \leq \frac{G'}{(G'' + G')} \leq 0.98, \text{ preferably } 0.5 \leq \frac{G'}{(G'' + G')} \leq 0.98.$$

The product according to the invention can be manufactured in predefined physical forms, or structures, such as a particle, a fibre, a string, a strand, a net, a film, a disc or a bead. It is preferred that the shape has an extension of less than 5 mm, preferably less than 1 mm, and larger than 0.5 mm or even larger than 0.8 mm when the HA substrate is in swollen form in physiological saline. A preferred shape is particles or beads having a size of 0.1-5.0 mm, such as 0.5-1 mm, when fully swollen in physiological saline.

According to one embodiment of the invention, a cross-linked HA gel product may be useful as a drug delivery device and be used in a method of drug delivery.

The cross-linked HA product according to the invention is useful for hydrating and/or vitalizing the skin. For this purpose, the product may e.g. be injected into the skin or included in a cream which is applied to the skin.

The cross-linked HA product according to the invention is useful in cosmetic or medical surgery. Non-limiting examples of cosmetic surgery are dermal filling, body contouring and facial contouring, in particular facial contouring. Non-limiting examples of medical surgery are dermal filling, body contouring, prevention of tissue adhesion, orthopaedic applications, incontinence treatment, treatment of vesicoureteral reflux (VUR), and formation of channels for draining purposes, e.g. in ophthalmology, and for keeping tissues apart.

According to one aspect, the present invention provides a method of treatment of a subject undergoing cosmetic or medical surgery, involving administration of a cross-linked HA product according to the invention to a subject in need thereof. Non-limiting examples of medical surgery are dermal filling, body contouring, prevention of tissue adhesion, orthopaedic applications, e.g. hip and joint therapy, and formation of channels for draining purposes, e.g. in ophthalmology, and for keeping tissues apart The desired shape and size is arranged during the manufacturing of the product, i.e. by arranging the substrate in a desired shape prior to the finalizing cross-linking. Another suitable way of obtaining a desired structure size involves manufacturing a cross-linked HA gel product at a desired concentration and subjecting the gel to mechanical disruption, such as mincing, mashing or passing the swollen or partly swollen gel, or the precipitated cross-linked product, through a filter or mesh with suitable pore size. The resulting gel particles or pieces are dispersed in a physiological salt solution, resulting in a gel dispersion or slurry with particles of desired size and shape. Depending on the shape, the size of a gel structure may be determined in any suitable way, such as by laser diffraction, microscopy, filtration, etc, and is decided by the longest distance between two ends of the particle. For spherical structures, the diameter equals the size for this purpose.

Useful gel structure size ranges and shapes depend on the intended application. For soft tissue augmentation, preferably subcutaneous administration, submuscular administration or supraperiostal administration, gel particles, pieces or fibres having a size, when subjected to a physiological salt solution, of more than 0.1 mm are useful. The term "soft tissue augmentation", as used herein, refers to any type of volume augmentation of soft tissues, including, but not limited to, facial contouring (e.g. more pronounced cheeks or chin), correction of concave deformities (e.g. post-traumatic, HIV associated lipoatrophy) and correction of deep age-related facial folds. Thus, soft tissue augmentation may be used solely for cosmetic purposes or for medical purposes, such as following trauma or degenerative disease. These two purposes are easily distinguished by the skilled person. The term "soft tissue", as used herein, refers to tissues that connect, support, or surround other structures and organs of the body. Soft tissue includes muscles, fibrous tissues and fat. Soft tissue augmentation may be performed in any mammal, including man. It is preferred that that the method is performed in a human subject.

The terms "subepidermal administration" or "subcuticular administration", as used herein, refer to administration beneath the epidermis of the skin, including administration into the dermis, subcutis or deeper, such as submuscularly or into the periosteum where applicable (in the vicinity of bone tissue).

Administration of gel structures may be performed in any suitable way, such as via injection from standard cannulae and needles of appropriate sizes or surgical insertion, e.g. in the case of administration of a film. The administration is performed where the soft tissue augmentation is desired, such as the chin, cheeks or elsewhere in the face or body. It is preferred to utilize the gel and the gel structures in facial contouring.

An implant according to the invention may be an aqueous composition comprising the cross-linked HA product according to the invention, e.g. in the shape of ≥0.1 mm large HA gel structures, such as particles, beads, fibres or cut-out stripes, and optionally a buffering agent and/or a tonicity agent. The composition may typically contain a physiological salt buffer. The composition may further comprise other suitable active substances and medical compounds, such as local anaesthetics (e.g. lidocaine hydrochloride), anti-inflammatory drugs, antibiotics and other suitable supportive medications, e.g. bone growth factors or cells. The cross-linked HA product according to the invention, or an aqueous composition thereof, may be provided in a pre-filled syringe, i.e. a syringe that is pre-filled with a sterilized, cross-linked HA product or an sterilized aqueous composition comprising the shaped product. Optionally, the cross-linked HA product may be kept in precipitated form in a syringe, bag or other suitable container and be brought to its non-precipitated form prior to injection or in the body following injection thereof.

It is preferred that the swelled or partly swelled, cross-linked HA product is autoclavable, since this is the most convenient way of sterilising the final product. This allows for preparation of a sterile, cross-linked HA product.

It goes without saying that the size of the gel structures, e.g. fibres, according to the invention is dependent upon how much the gel has been allowed to swell, and the ionic strength of the buffer, solution or carrier that is included in and/or surrounding the gel structures. Throughout this specification, given structure sizes assume physiological conditions, particularly isotonic conditions. It shall be noted that, while it is preferred that the gel structures contain and are dispersed in a physiological salt solution, it is contemplated that the gel structures according to the invention can temporarily be brought to different sizes by subjecting the gel structures to a solution of another tonicity, different pH or if the gel structures have not been allowed to swell to their maximum size.

As used herein, a physiological, or isotonic, solution is a solution having an osmolarity in the range of 200-400 mOsm/l, preferably 250-350 mOsm/l, more preferably approximately 300 mOsm/l.

The cross-linked HA gel product according to the invention is stable, but not permanent, under physiological conditions. According to an embodiment of the invention, at least 70%, preferably at least 90%, of the cross-linked HA gel product remains for at least two weeks in vivo, more preferably between two weeks and two years. The term "degraded" implies that less than 20%, preferably less than 10%, of the medium remains in the body.

The cross-linked HA gel product according to the invention is more resistant to biodegradation in vivo than natural HA, but also to commercially available cross-linked HA gel products, c.f. Examples 8 and 9. The prolonged presence of the stable gel product is advantageous for the patient, since the time between treatments is increased. It is also important that the product is highly similar to native HA, in order to maintain the high biocompatibility of the native HA.

DEFINITIONS

Throughout this disclosure, the terms below are defined as follows.

| Term | Property | Meaning |
| --- | --- | --- |
| HA | | HA refers to sodium hyaluronate |
| Gel-form HA | | Gel-form HA is the cross-linked HA that cannot be extracted from the gel by rinsing with e.g. saline, as opposed to the extractable HA |

| Term | Property | Meaning |
|---|---|---|
| Extractable HA | | Extractable HA is the HA, cross-linked or not cross-linked, that can be extracted by rinsing with e.g. saline |
| $C_{HA}$ | HA concentration | $C_{HA} = \dfrac{m_{HA}}{m_{sample}}$ or $C_{HA} = \dfrac{m_{HA}}{V_{sample}}$<br>Expressed in mg/g, mg/mL, % (w/w), % (w/v) |
| SwD | Swelling Degree | SwD is preferably expressed in g/g, mL/g, or as a dimensionless number. SwD is the inverted concentration of gel-form HA in a gel that is fully swollen in 0.9% saline, i.e. the volume, or mass, of fully swollen gel that can be formed per gram dry cross-linked HA. SwD describes the maximum liquid-absorbing (0.9% saline) capability of the product. |
| $C_{min}$ | Minimum HA Concentration | Concentration of gel-form HA in a gel that is fully swollen in 0.9% saline, normally expressed in mg/g or mg/mL.<br>$c_{min} = \dfrac{1}{SwD \times 0.001}$ |
| GelC | Gel Content | $GelC = \dfrac{m_{HA\ in\ gel\text{-}form}}{m_{HA\ total}}$<br>Expressed as g/g, a dimensionless number, or %. The Gel Content is the proportion of HA that is bound in gel-form out of the total HA content in the product. |
| MoD | Degree of Modification | $MoD = \dfrac{n_{bound\ crosslinking\ agent}}{n_{disaccharide\ units}}$<br>Expressed as mole/mole, a dimensionless number, or mole %. MoD describes the amount of cross-linking agent(s) that is bound to HA, i.e. molar amount of bound cross-linking agent(s) relative to the total molar amount of repeating HA disaccharide units. MoD reflects to what degree the HA has been chemically modified by cross-linking agent(s). |
| CrR | Effective Cross-linker ratio | $CrR = \dfrac{n_{HA-X-HA}}{n_{HA-X-HA} + n_{HA-X}}$<br>where X is a cross-linking agent. CrR can also be expressed as:<br>$CrR = \dfrac{\#crosslinked\ crosslinking\ agents}{\#bound\ crosslinking\ agents}$<br>Expressed in mole/mole, a dimensionless number, or mole %. CrR describes the proportion of total bound cross-linking agent (HA—X—HA and HA—X) that has bound two (or more) disaccharides (only HA—X—HA). |
| MoE | Modification Efficiency | $MoE = \dfrac{C_{min}}{MoD}$<br>MoE is a dimensionless number obtained as the ratio between $C_{min}$ expressed in mg/g and MoD expressed in %. MoE describes the amount of interconnections, caused both by chemical modification and from molecular entanglements, which have been achieved at the cost of a certain degree of chemical modification by cross-linking agent(s). Example: MoE for a product with $C_{min}$ = 35 mg/mL and MoD = 1.15% is approximately 30, and is calculated as follows:<br>$MoE = \dfrac{35}{1.15} \approx 30$ |
| G' | Elastic modulus | The elastic modulus describes the resistance of the gel to elastic deformation, and is expressed in Pa (Pascal). A strong gel will give a larger number compared to a weak gel. |
| G'' | Viscous modulus | The viscous modulus describes the resistance of the gel to viscous deformation, and is expressed in Pa (Pascal). Together with G', it describes the total resistance to deformation. |

Without desiring to be limited thereto, the present invention will in the following be illustrated by way of examples.

EXAMPLES

Analytical Methods
Determination of HA Concentration

The method for determination of HA content is adopted from the assay test for sodium hyaluronate described in Ph. Eur. 1472. The principle for the method is that a condensation reaction of the furfural derivatives formed by heating in sulphuric acid occurs with the carbazole reagent, forming a purpur colored product. The reaction is specific for the D-glucuronic acid part of HA. The absorbance is measured at 530 nm and glucuronic acid is used for standardization.

The product formed from the content of D-glucuronic acid (GlcA) in the sample is determined by reaction with carbazole. To get homogeneous sample solutions, the stabilized gel of HA is degraded with sulphuric acid at 70° C. and diluted with 0.9% NaCl-solution. The solutions are mixed with sulphuric acid at 95° C. and thereafter with carbazole reagent. The reactions result in pink coloured solutions. The intensity of the colour is measured with a colorimeter at 530 nm, and the absorbance of each sample is directly proportional to the GlcA-content. The HA content is calculated from the GlcA-content in each sample.

Determination of Gel Content (GelC)

GelC describes in % the proportion of the total HA that is bound in gel form. Gel content is defined as the amount of HA in a sample that does not pass through a 0.22 μm filter. GelC is calculated from the amount of HA that is collected in the filtrate, here denoted extractable HA. The gel content and the extractable HA content are given in percent of the total amount of HA in the gel sample. In short, the gel content is determined by mixing a certain amount of gel sample with 0.9% NaCl in a test tube. The gel is allowed to swell where after the NaCl-phase is separated from the gel-phase by filtration through a 0.22 μm filter. The concentration of HA in the filtrate is determined according to the procedure for determination of HA concentration.

Determination of Swelling Degree (SwD)

SwD describes the liquid-absorbing capability of a HA hydrogel product, i.e. its capability to absorb 0.9% NaCl, and is reported as the weight (in gram) of the resulting fully swollen gel per gram of HA. The product is typically a partly swollen, cross-linked HA gel, but could also be present in the dry state. SwD can be determined from the swelling factor (SwF). SwF is measured as the volume (V) of fully swollen gel that is formed upon swelling a certain weight (w) of a partly swollen product in saline in a measuring cylinder, and calculated as:

$$SwF = \dfrac{V_{fully\ swollen\ gel}}{W_{partly\ swollen\ gel}}$$

SwD is then calculated as:

$$SwD = \frac{SwF}{[HA] \times GelC \times 0.01}$$

where [HA] is the HA concentration (in g/mL gel) of the partly swollen gel and GelC is the gel content (in %). The GelC is included in the formula to correct for extractable HA content which will not contribute to the swelling of the gel. It is assumed that the density of the fully swollen gel is 1.0 g/mL.

Notably, a stronger gel will have a lower SwD, while a weaker gel will have a higher SwD.

Determination of Minimum Concentration ($C_{min}$)

$C_{min}$ (or $c_{min}$) describes the concentration of gel-form HA in a cross-linked HA gel product, fully swollen in 0.9% NaCl, after all extractable HA is removed. Since the product cannot absorb more liquid, this concentration is the minimum HA concentration that can be obtained for this particular gel product. Notably, a stronger gel will have a higher $C_{min}$, while a weaker gel will have a lower $C_{min}$.

The $C_{min}$ (in mg/mL or mg/g) is determined in analogy with the determination of SwD as set out above, using the relation:

$$c_{min} = \frac{1}{SwD \times 0.001} C_{min} = \frac{1}{SwD}.$$

Determination of Degree of Modification (MoD)

MoD describes the molar amount of bound cross-linking agent(s) relative to the total number of repeating HA disaccharide units (Kenne et al., Carbohydrate Polymers 91 (2013) 410-418). This measure does not distinguish between mono-linked and actually cross-linked cross-linking agent(s), i.e. all cross-linking agent(s) that is bound to HA via at least one covalent bond is included. For instance, a MoD of 1% for a HA gel cross-linked with BDDE means that there is 1 bound (mono-linked or cross-linked) molecule of BDDE per 100 disaccharide units in the HA gel.

MoD is determined using NMR spectroscopy on enzymatically degraded gel product. Soluble HA, residual (non-bound) cross-linking agent(s) and derivatives thereof are washed away prior to the degradation of the gel by filtration on a 0.22 μm filter. The gel product is degraded at 37° C. by enzymatic treatment using chondroitinase. The degraded gel product is subjected to NMR spectroscopy by recording one-dimensional $^1$H NMR spectra on a 500 MHz spectrometer, equipped with a standard 5 mm probe.

The NMR spectra are evaluated by integration of the signal at $\delta_H$ 1.6 ppm, which origins from four protons in the linked BDDE molecule, and the signals at δH 2.0 ppm, which is from the three protons in the $CH_3$ groups on the N-acetylglucosamine residues of the HA disaccharides. The ratio between the integrals for these two signals is proportional to the ratio between the molar amount of bound BDDE and disaccharides after correction for the number of protons responsible for each signal, hence giving MoD.

$$MoD = \frac{n_{bound\ crosslinking\ agent}}{n_{disaccharide\ units}}$$

Determination of Modification Efficiency (MoE)

MoE is the ratio between the minimum HA concentration and the degree of modification of a gel, i.e.:

$$MoE = \frac{c_{min}}{MoD} = \frac{1}{SwD \times 0.001 \times MoD}$$

$C_{min}$ (mg/g or mg/mL) and MoD (%) are determined as described previously. Since $C_{min}$ is closely related to the strength of a gel, MoE is a measure of how efficient the cross-linking procedure is in producing a gel of desired strength. A process with a high MoE will produce a gel with a high $C_{min}$ and a low MoD, i.e. a strong gel is produced despite limited chemical modification of the HA.

Determination of Effective Cross-linker ratio (CrR)

CrR describes the proportion of total bound cross-linking agent(s) (HA-X-HA and HA-X) that has bound two (or more) disaccharides (only HA-X-HA):

$$CrR = \frac{n_{HA-X-HA}}{n_{HA-X-HA} + n_{HA-X}}$$

where X is a cross-linking agent.

The method is based on determination of HA-X fragments using LC-MS following degradation of the HA gel using chondroitinase AC from Arthrobacter aurescens or chondroitinase ABC from *Proteus vulgaris* into fragments consisting of the main disaccharide (Δdi-HA) and fragments with bound cross-linking agent (HA-X) containing 1-8 disaccharides. The fragments are separated using size exclusion chromatography (SEC), and detected using mass spectrometry (MS). The peak areas for each group of fragment are summed. and CrR is calculated as:

$$CrR = \frac{\text{Peak area}_{HA-X-HA}}{\text{Peak area}_{HA-X-HA} + \text{Peak area}_{HA-X}}$$

It is assumed that all types of HA-X fragments have the same response in the MS detector, i.e. a certain peak area corresponds to a given molar amount for all types of HA-X fragments (Kenne et al., Carbohydrate Polymers 91 (2013) 410-418).

When determining CrR, care should be taken to only include BDDE bound by ether linkages. Depending on the conditions during cross-linking, BDDE can bind to the HA via both ether and ester linkages. Since the ester linkages are easily hydrolyzed, it is only the ether-bound BDDE that will contribute to the gel strength and duration in the long term. The fragments with ester-bound BDDE have the same mass as the ether-bound BDDE but can be detected as they have slightly different chromatographic retention times. To determine the CrR without any ester-bound BDDE, the samples should be hydrolyzed before analysis. Hydrolysis of the samples could e.g. be made by adding base and/or heat before or after the enzymatic degradation.

While the method for determining CrR has now been described using BDDE cross-linked HA as an illustrative example, it is in no way limited to this specific combination of cross-linker and polysaccharide. The method may readily be adapted for any other polyfunctional cross-linking agent using the principles outlined in (Kenne et al., Carbohydrate Polymers 91 (2013) 410-418) and correcting/adapting the masses of the HA-X and HA-X-HA fragments in the LC-MS aquisition method for the specific cross-linking agent used.

Rheometry

Rhemometry in the oscillating mode is used to determine the viscoelastic properties of the swelled gel product. The elastic modulus (G') describes the gel strength in terms of the gels physical resistance to elastic deformation. The viscous modulus (G") describes the gel strength in terms of the gel's physical resistance to viscous deformation. The measurement is performed using an oscillating rheometer.

Rheometry measurements are performed as follows. Frequency sweeps are made with a resting time of at least 15 minutes between sample loading and measurement, and a strain (γ) of 0.1%. A parallel plate probe with a diameter of 25 mm is used with a gap of 1 or 2 mm. Average values of the elastic modulus (G') and viscous modulus (G") are evaluated at 0.1 and 1 Hz from the frequency sweeps. Amplitude sweeps are made at 1 Hz to verify that the frequency sweep was performed at a strain (γ) within the linear viscoelastic range.

EXAMPLES

Example 1

1 g HA was dissolved in 7 g 0.25 M NaOH. After the HA had dissolved, 50 mg BDDE mixed with 0.2 g 0.25 M NaOH was added. The initial cross-linking reaction was allowed to take place for 2 h at 50° C. The activated HA was passed through a metal mesh, and was allowed to swell in 30 g water for a short period of time. The swelled gel was precipitated in ethanol and washed 3 times with an ethanol/water/NaOH mixture. The cross-linking was allowed to finalize in a solution of ethanol and NaOH for 2 h at 50° C. The ethanol concentration was about 70 wt %, and the NaOH concentration 50 mM. Neutralization was performed with HCl to an apparent pH of 7. The precipitate was washed and dried.

The resulting dry powder was allowed to swell into a gel in buffered 0.9% NaCl to a HA concentration of 20 mg/mL. The gel was filled into syringes and autoclaved.

A reference gel was made using the above method without the precipitation and final cross-linking in the ethanol mixture.

MoD and CrR were analysed. Both gels had a MoD of 3.4%. CrR for the reference was 0.1, and it was 3 times higher for the gel which had been finally cross-linked in precipitated form.

Example 2

Comparative Experiments

Cross-linked HA products were prepared in four different ways A-D:
- (A): A cross-linked HA film was made according to Example 24 in WO 87/07898. Sodium hyaluronate (3% w/v) was mixed with 0.75% (v/v) NaOH. 1,4-butanediol diglycidyl ether (BDDE) was added to a concentration of 0.22% (w/v) and allowed to react for 24 h. The mixture was dialysed against running distilled water for 24 h. Ammonia (25% v/v) was added to the dialysed mixture, and the mixture was poured into a petri dish of polystyrene. It was kept for drying for 2 days at room temperature. A transparent, planar, water-insoluble film was obtained. The film was then divided into particles, swelled in saline, filled into a syringe and autoclaved.

The variants (B) to (D) were made to demonstrate how the difference between the drying processes as described in WO 87/07898, corresponding to variant (B), and the more effective cross-linking process according to the invention involving a precipitation step, variants (C) and (D). The same MoD was achieved in all variants (B)-(D).
- (B): The first cross-linking step was using a BDDE concentration of 0.22% and a NaOH concentration of 0.75%. Dialysis, addition of ammonia and drying were performed as set out in variant (A). The resulting film looked as in variant (A) and was treated the same way. The resulting particles were swelled in saline, filled into a syringe and autoclaved.
- (C): First cross-linking as in variant (B). Dialysis was performed as set out in variant (A). The gel was precipitated in ethanol and a second, finalizing cross-linking was performed in an aqueous solution of 70% EtOH and 0.23% NaOH. The particles were swelled in saline, filled into a syringe and autoclaved.
- (D): Manufacturing process as in variant (C), but exchanging the dialysis step with a washing step after precipitation to eliminate any unreacted cross-linker molecules.

The effective cross-linker ratio (CrR) was determined for the resulting HA particles from each experiment A-D, as shown in Table 1.

TABLE 1

| Analysis | Sample | | | |
| --- | --- | --- | --- | --- |
|  | A | B | C | D |
| CrR | 0.1 | 0.2 | 0.5 | 0.6 |

It can be concluded that replacing the drying step in experiments A and B with a final cross-linking of HA in precipitated form (C-D) drastically increases the CrR up to sixfold without increasing the MoD. This implies that the efficiency of the overall cross-linking procedure is greatly enhanced, since a larger number of the covalently incorporated cross-linking agents are involved in actual cross-linking of the HA. It is also evident that replacing the dialysis of experiments A-C with washing of the HA in precipitated form (D) further increases the CrR, again without increasing the MoD.

Example 3

Cross-Linking Agent Concentrations in Initial Cross-Linking Step

An initial step of cross-linking HA with BDDE was performed. In the reference sample (Ref), no further precipitation step or cross-linking of precipitated HA was performed. The following samples were also prepared:
- (A): BDDE and HA concentrations same as reference, but with cross-linking of activated HA in precipitated form
- (B): As A, but with BDDE=2/3*A
- (C): As A, but with BDDE=1/3*A The finalizing cross-linking step occurred in 70% EtOH containing 50 mM NaOH, at 23° C. for 45 h. The particles from each sample were swelled in saline, filled into a syringe and autoclaved. The degree of modification (MoD), effective cross-linker ratio (CrR), swelling (SwD) and gel content were determined for the resulting HA particles from each experiment A-D, as shown in Table 2.

TABLE 2

| Analysis | Sample | | | |
|---|---|---|---|---|
| | Ref | A | B | C |
| MoD | 1.0 | 1.0 | 0.7 | 0.4 |
| CrR | 0.2 | 0.6 | 0.6 | 0.6 |
| SwD | 130 | 50 | 110 | 240 |
| Gel content | 85 | 98 | 90 | 75 |

It is evident that the inclusion of a finalizing cross-linking step in variant (A) yields a stronger gel (lower swelling) and higher CrR than the reference sample. Decreased concentrations of cross-linking agent in the initial cross-linking step maintains the high CrR and provides a loser gel (higher swelling), but with a decrease in gel content.

Example 4 pH in Finalizing Cross-linking Step

An initial step of cross-linking HA with BDDE was performed. In the reference sample (Ref), no further precipitation step or cross-linking of precipitated HA was performed. The following samples were also prepared:
- (A): Finalizing cross-linking step in 70% EtOH without addition of NaOH, 23° C. for 45 h.
- (B): Finalizing cross-linking step in 70% EtOH containing 50 mM NaOH, 23° C. for 45 h.

The particles from each experiment were swelled in saline, filled into a syringe and autoclaved. The degree of modification (MoD), effective cross-linker ratio (CrR), swelling (SwD) and gel content were determined for the resulting HA particles from each experiment A-C, as shown in Table 3.

TABLE 3

| Analysis | Sample | | |
|---|---|---|---|
| | Ref | A | B |
| MoD | 0.9 | 0.9 | 1.0 |
| CrR | 0.2 | 0.3 | 0.6 |
| SwD | 130 | 110 | 50 |
| Gel content | 87 | 95 | 98 |

It is shown that performing a final cross-linking of HA in precipitated form (A-B) increases the CrR without increasing the MoD, in particular when NaOH was added (B). In addition, the gel content of the resulting product is increased with a final cross-linking of HA in precipitated form, indicating that it enhances the efficiency of the overall cross-linking procedure.

Example 5

Precipitant Concentration and pH in Finalizing Cross-linking Step

An initial step of cross-linking HA with BDDE was performed. In the reference sample (Ref), no further precipitation step or cross-linking of precipitated HA was performed. Samples A-E were prepared with a finalizing cross-linking step at 23° C. for 45 h with 60-90% (vol/vol) EtOH and 30-70 mM NaOH, as set out in Table 4.

The particles from each of the experiments were swelled in saline, filled into a syringe and autoclaved. The degree of modification (MoD) and effective cross-linker ratio (CrR) were determined for the resulting HA particles from each experiment A-E, as shown in Table 4.

TABLE 4

| Parameter | Sample | | | | | |
|---|---|---|---|---|---|---|
| | Ref | A | B | C | D | E |
| EtOH (%) | NA | 60 | 70 | 70 | 70 | 90 |
| NaOH (mM) | NA | 50 | 30 | 50 | 70 | 50 |
| MoD | 0.6 | 0.6 | 0.7 | 0.6 | 0.6 | 0.7 |
| CrR | 0.24 | 0.6 | 0.6 | 0.6 | 0.6 | 0.6 |

It is concluded that the effective cross-linker ratio is independent of precipitant (ethanol) concentration and pH (NaOH concentration) in the finalizing cross-linking step.

Example 6

Time and Temperature in Finalizing Cross-linking Step

An initial step of cross-linking HA with BDDE was performed. The activated HA was precipitated, and the finalizing cross-linking step was performed in 70%EtOH and 50 mM NaOH at 23° C. or at 35° C., and allowed to proceed for up to 48 h. The resulting particles were swelled in saline, filled into a syringe and autoclaved.

As shown in FIG. 3, the effective cross-linker ratio was determined for the resulting HA particles from different reaction times and temperatures. It is concluded that the effective cross-linker ratio is not particularly affected by the temperature and reaches a plateau after less than 20 h.

Example 7

Crosslinking ratio (CrR) of Commercially Available HA-gels (Comparative)

CrR for a number of commercially available gels was determined as set out in the Analytical methods section above.

TABLE 5

| Product | Manufacturer | CrR |
|---|---|---|
| Restylane | Q-Med/Galderma | ~0.2 |
| Yvoire Classic | LG | ~0.3 |
| Teosyal Deep Lines | Teoxane | ~0.1 |
| Juvederm Ultra 2 | Allergan | ~0.1 |
| Esthelis Basic | Anteis | ~0.1 |
| Stylage M | Vivacy | ~0.1 |
| Juvederm Voluma | Allergan | ~0.1 |
| Emervel Classic | Galderma | ~0.1 |

As a comparison, the cross-linked HA products according to the invention display a CrR of 0.35 or higher, such as in the range of 0.35-0.8. It is concluded that the manufacturing process according to the present invention provides a new range of HA gel products with high CrR values.

Example 8

Heat Degradation Rate of HA gels

The heat degradation rate was determined for a HA gel sample manufactured according to example 3B above. As a reference, the commercially available product Restylane from Q-Med/Galderma was used. The experiments were performed in duplicate. The CrR of the sample was 0.6 and of the reference 0.2.

The sample and the reference were transferred into vials and stored at 90° C. At different time points, one vial of the sample and one vial of the reference were cooled to room temperature and analyzed for gel content. The results of the heat-induced gel degradation are shown in FIG. 4, wherein the values from the sample gel made according to example 3B are denoted by the symbol (▲) and the corresponding Restylane reference values are denoted by the symbol (x).

It is concluded that the degradation rate is slower for the sample with the high CrR compared to the reference with a factor of about 2. A gel made according to example 3B would thus have an expected duration in vivo of about twice that of the reference.

Example 9

Peroxyl Radical-induced Degradation Rate of HA gels

A gel sample was manufactured according to example 6. The temperature in the finalizing cross linking step was 35° C. for 24 h. As a reference, the commercially available product Restylane from Q-Med/Galderma was used. The CrR of the sample was 0.5 and that of the reference 0.2.

The radical degradation rate was determined for the gel and reference samples. The experiments were made in duplicate. The radical degradation rate was determined by dispersing 0.25 g gel in 10 ml phosphate buffered saline. A radical generator, 2,2'-azobis-2-methyl-propanimidamide, dihydrochloride, was added to a concentration of 10 mM, and the reaction was performed at 37° C. The HA content of the supernatant was determined at different time points. The gel content was calculated from the initial weight of the gel and the HA content in the supernatant at the different time points. The result of the peroxyl radical-induced degradation is shown in FIG. 5, wherein the values from the sample gel made according to example 6 are denoted by the symbol (■) and the corresponding Restylane reference values are denoted by the symbol (x).

It is concluded that the degradation rate is slower for the sample with the high CrR compared to the reference with a factor of about 2. A gel made according to example 6 with an effective cross-linker ratio of 0.5 would thus have an expected duration in vivo of about twice that of the reference.

The invention claimed is:

1. A process for manufacturing a cross-linked hyaluronic acid (HA) product, comprising:
    (a) initiating cross-linking of HA by reacting HA with one or more polyfunctional cross-linking agents in an aqueous solution to obtain an activated HA;
    (b) removing unreacted cross-linking agent(s) from the activated HA; and
    (c) finalizing the cross-linking of the activated HA by subjecting the activated HA to further cross-linking conditions without addition of any additional cross-linking agent to obtain a cross-linked HA product;
    wherein the finalizing cross-linking step (c) is performed in a suspension of a liquid precipitating medium and the activated HA in precipitated form.

2. A process according to claim 1, wherein the removing step (b) comprises:
    (b1) precipitating the activated HA in a liquid precipitating medium to obtain a suspension comprising the liquid precipitating medium and the activated HA in precipitated form; and
    (b2) removing unreacted cross-linking agent(s) from the suspension of precipitated, activated HA.

3. A process according to claim 2, wherein the removing substep (b2) comprises washing the precipitated, activated HA with a liquid precipitating medium.

4. A process according to claim 1, wherein the finalizing cross-linking step (c) comprises:
    (c1) precipitating the activated HA in a liquid precipitating medium to obtain a suspension comprising the liquid precipitating medium and the activated HA in precipitated form; and
    (c2) finalizing the cross-linking of the activated HA by subjecting the suspension of precipitated, activated HA to further cross-linking conditions without addition of any additional cross-linking agent to obtain a cross-linked HA product.

5. A process according to claim 1, wherein the liquid precipitating medium contains more than 65 wt % of a water-soluble organic solvent.

6. A process according to claim 5, wherein the water-soluble organic solvent is ethanol.

7. A process according to claim 1, wherein the initial cross-linking step (a) provides an activated HA in gel form.

8. A process according to claim 1, wherein the cross-linking agent is selected from the group consisting of divinyl sulfone, multiepoxides and diepoxides.

9. A process according to claim 1, wherein the cross-linking agent is 1,4-butanediol diglycidyl ether (BDDE).

10. A process according to claim 1, further comprising the steps of:
    (d) subjecting the precipitated, cross-linked HA product from step (c) to non-precipitating conditions; and
    (e) isolating the cross-linked HA product in non-precipitated form.

11. A process according to claim 1, comprising a step of sterilizing the cross-linked HA product.

12. The process according to claim 1, comprising the preparation of a desired shape of the activated HA obtained in step (a) prior to the final cross-linking in step (c).

13. The process according to claim 12, wherein the preparation of a desired shape of the activated HA obtained in step (a) occurs prior to the removing of unreacted cross-linking agent(s) from the activated HA in step (b).

14. The process according to claim 12, wherein the desired shape is particles having a size of 0.1 - 5.0 mm.

15. The process according to claim 12, wherein the desired shape is a string, a net, or a film.

16. The process according to claim 12, wherein the desired shape is a string, said string having a ratio between its length and its width of 5:1 or higher.

* * * * *